(12) United States Patent
Ghiani et al.

(10) Patent No.: US 10,251,960 B2
(45) Date of Patent: Apr. 9, 2019

(54) FLUORESCENT SOLID LIPID NANOPARTICLES COMPOSITION AND PREPARATION THEREOF

(71) Applicant: BRACCO IMAGING S.P.A., Milan (IT)

(72) Inventors: Simona Ghiani, Almese (IT); Alessandro Maiocchi, Monza (IT); Lara Caminiti, Occhieppo Superiore (IT); Luigi Miragoli, Dovera (IT)

(73) Assignee: BRACCO IMAGING S.P.A., Milan (IT)

( * ) Notice: Subject to any disclaimer, the term of this patent is extended or adjusted under 35 U.S.C. 154(b) by 472 days.

(21) Appl. No.: 14/894,505

(22) PCT Filed: May 28, 2014

(86) PCT No.: PCT/EP2014/061082
§ 371 (c)(1),
(2) Date: Nov. 28, 2015

(87) PCT Pub. No.: WO2014/191467
PCT Pub. Date: Dec. 4, 2014

(65) Prior Publication Data
US 2016/0106869 A1    Apr. 21, 2016

(30) Foreign Application Priority Data

May 30, 2013  (EP) ..................................... 13169851

(51) Int. Cl.
| | |
|---|---|
| A61B 5/00 | (2006.01) |
| A61B 8/00 | (2006.01) |
| A61B 10/00 | (2006.01) |
| A61K 49/00 | (2006.01) |
| A61K 9/51 | (2006.01) |
| A61K 9/10 | (2006.01) |

(52) U.S. Cl.
CPC ...... *A61K 49/0093* (2013.01); *A61K 49/0034* (2013.01); *A61K 49/0052* (2013.01); *A61K 49/0054* (2013.01); *A61K 49/0078* (2013.01); *A61K 9/10* (2013.01); *A61K 9/5123* (2013.01); *A61K 49/0032* (2013.01)

(58) Field of Classification Search
None
See application file for complete search history.

(56) References Cited

U.S. PATENT DOCUMENTS

| | | |
|---|---|---|
| 2005/0079131 A1 | 4/2005 | Lanza et al. |
| 2006/0018830 A1 | 1/2006 | Cappelletti et al. |
| 2006/0083781 A1 | 4/2006 | Shastri et al. |
| 2011/0117015 A1 | 5/2011 | Rossello et al. |
| 2012/0294809 A1* | 11/2012 | Walters ..................... C07F 5/00 9/14 |

FOREIGN PATENT DOCUMENTS

| | | |
|---|---|---|
| WO | 2003/057259 A2 | 7/2003 |
| WO | 2010/018216 A2 | 2/2010 |
| WO | 2012/109755 A1 | 8/2012 |
| WO | 2013/135750 A1 | 9/2013 |
| WO | 2014/037498 A2 | 3/2014 |

OTHER PUBLICATIONS

Brücher et al. (Inorgica Chinnica Acta 1996, 249, 191-199).*
Zhu et al. (J. Nanosci. Nanotech. 2006, 6, 996-1003).*
Hu et al. (J. Pharm. Pharmacol. 2004, 56, 1527-1535).*
Sharma et al. (Advanced Powder Techno. 2007, 18, 663-698).*
Texier et al. (Molecules 2012, 17, 5564-5591).*
Bao et al. (Bioconj. Chem. 2012, 23, 1322-1332).*
Achilefu, S., "Lighting up tumors with receptor-specific optical molecular probes," Technology in Cancer Research & Treatment, 2004, 3:393-408.
Office Action for Chinese application No. 201480037003.0, dated Jun. 2, 2017 (English Translation).
Office Action for Japanese application No. 2016-516152, dated Jun. 6, 2017 (English Translation).

(Continued)

*Primary Examiner* — Michael G. Hartley
*Assistant Examiner* — Melissa J Perreira
(74) *Attorney, Agent, or Firm* — Vivicar Law, PLLC

(57) ABSTRACT

The present invention discloses a solid lipid nanoparticle (SLN) comprising: a) a solid lipid core comprising at least a glyceride and/or at least a fatty acid; b) a mixture of amphiphilic components forming a shell around said core a); c) an alkaline-earth complex with a compound of formula I and/or II: d) at least a fluorescent dye selected from: a cyanine fluorescent dye and/or a polyetherocyclic compound selected from: coumarin, pyrano, quinoline, pyranoquinoline, indole and pyranoindole derivates in acid form or a pharmaceutically acceptable salt thereof. These nanoparticles allow a prolonged blood circulation half-life, show enhanced photostability and improved fluorescence signal. The dye is preserved from degradation and improves the fluorescent quantum yield.

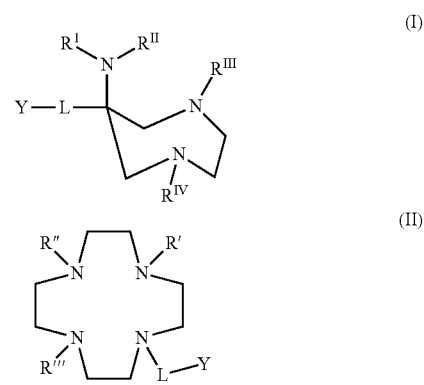

23 Claims, 9 Drawing Sheets

(56) References Cited

OTHER PUBLICATIONS

Morel, et al., "NMR relaxometric investigations of solid lipid nanoparticles (SLN) containing gadolinium (III) complexes," European Journal of Pharmaceutics and Biopharmaceutics, 1998, vol. 45, pp. 157-163.
Zheng et al., "Enhanced tumor treatment using biofunctional indocyanine green-containing nanostructure by intratumoral or intravenous injection," Mol. Pharmaceutics, 2012, vol. 9, pp. 514-522.
Altinoglu et al., "Near infrared imaging with nanoparticles," WIREs Nanomedicine and Nanobiotechnology, vol. 2, 2010, pp. 461-477.
Anelli et al., "Mixed micelles containing lipophilic gadolinium complexes as MRA contrast agents," MAGMA, 2001, vol. 12, pp. 114-120.
Chapman, D., "The polymorphism of glycerides," Chem. Rev., 1962, pp. 433-456.
Cortesi et al., "Production of lipospheres as carriers for bioactive compounds," Biomaterials, 2002, 23:2283-2294.
European Search Report for European application No. 13169851.6, dated Oct. 24, 2013.
Garcia-Fuentes et al., "Design of lipid nanoparticles for the oral delivery of hydrophilic macromolecules," Colloids and Surfaces B: Biointerfaces, 2002, 27: 159-168.
Grange, et al., "Combined delivery and magnetic resonance imaging of neural cell adhesion molecule targeted doxorubicin-containing liposomes in experimentally induced Kaposi's sarcoma," Cancer Research, vol. 70, No. 6, 2010, pp. 2180-2190.
Greene, T.W., "Protective groups in organic synthesis," John Wiley & Sons, Inc., 1981, pp. 152-178.
Johnson, I., "Fluorophores for optical imaging," In: Optical Imaging of Cancer, Rosenthal, E. et al. (eds.), Springer Science+Business Media, LLC, New York, 2009, pp. 59-77.
Landsman, et al., "Light absorbing properties, stability and spectral stabilization of indocyanine green," J. Appl. Physiol., 1976, pp. 575-583.
Morel, et al., "Enhanced tumor treatment using biofunctional indocyanine green-containing nanostructure by intratumoral or intravenous injection," European Journal of Pharmaceutics and Biopharmaceutics, 1998, pp. 157-163.
Navarro, et al., "Cell tolerability and biodistribution in mice of Indocyanine green-loaded lipid nanoparticles," Journal of Biomedical Nanotechnology, 2012, vol. 8, pp. 594-604.
Navarro, et al. "Lipid Nanoparticle Vectorization of IndoCyanine Green Improves Fluorescence Imaging for Tumor Diagnosis and Lymph Node Resection," Journal of Biomedical Nanotechnology, 2012, vol. 8, pp. 730-741.
PCT Search Report and Written Opinion for PCT/EP2014/061082, dated Sep. 19, 2014.
Rolla, G., et al., "Paramagnetic solid lipid nanoparticles as a novel platform for the development of molecular MRI probes," Chemistry A European Journal, 2013, vol. 19, pp. 11189-11193.
Saxena, V., et al., "Enhanced photo-stability, thermal-stability and aqueous-stability of indocyanine green in polymeric nanoparticulate systems," Journal of Photochemistry and Photobiology B : Biology, 2004, 74:29-38.
Sawant, et al., "Recent Advances and Patents on Solid Lipid Nanoparticles," Recent Patents on Drug Delivery & Formulation, 2008, vol. 2, pp. 120-135.
Windbergs, et al., "Investigating the Principles of Recrystallization from Glyceride Melts," AAPS PharmaSciTech, 2009, vol. 10, pp. 1224-1233.
Zheng et al., "Indocyanine Green-Containing Nanostructure as Near Infrared Dual-Functional Targeting Probes for Optical Imaging and Photothermal Therapy," Mol. Pharmaceutics, 2011, vol. 8, pp. 447-456.

* cited by examiner

FLUORESCENT SOLID LIPID NANOPARTICLES COMPOSITION AND PREPARATION THEREOF

CROSS-REFERENCE TO RELATED APPLICATIONS

This application is the national stage application of corresponding international application number PCT/EP2014/061082, filed May 28, 2014, which claims priority to and the benefit of European application no. 13169851.6, filed May 30, 2013, all of which are hereby incorporated by reference in their entirety.

The present invention relates to the field of pharmaceutical and diagnostic compositions, in particular to compositions containing fluorescence probes, more in particular to solid lipid nanoparticles containing said probes.

The present invention also relates to the field of instrumental diagnostics, in particular real-time imaging-guided surgery.

BACKGROUND OF THE INVENTION

Indocyanine Green (herein also named ICG) is an FDA-approved fluorescent probe, but suffers of a fast metabolic clearance because it is rapidly eliminated by the liver. It is known that after intravenous injection, ICG is bound to albumin and subsequently taken up almost exclusively by the hepatic parenchymal cells. When ICG is administered at the human recommended dose of 0.5 mg/kg a normal blood half-time is around 3.0 minutes (Rosenthal E, Zinn K R, editors. Optical Imaging of Cancer: Clinical Applications. New York, N.Y., USA: Springer; 2009. pp 72). This efficient hepatobiliary excretion prevents the selective accumulation of ICG at specific pathological sites, limiting its possible clinical uses, which actually are mainly confined to optical examinations of blood flow with applications in ocular angiography, hepatic function characterization, or in the measurement of cardiac output.

Indocyanine Green is considered a promising candidate for high sensitive tumor detection and lymph nodes mapping in the clinical fluorescence imaging applications. Particularly wished is a formulation of ICG for use in the real-time visualization of cancerous lesions and sentinel lymph node detection during surgery lesions removal or endoscopic surgical treatments.

However, as said above, due to its very low residence time in human blood, ICG does not have any significant targeting property at the tumor tissue after intravenous administration, when used at the clinical recommended dose of 0.5 mg/kg.

Moreover, ICG is unstable in aqueous solution (already at µM concentration) and must be used within 6 hours due to its tendency to aggregate. The dye-dye interactions have adverse effects on the optical properties of ICG as the decreasing of the extinction coefficient and the fluorescence self-quenching effect after the dye excitation (Landsman, M. L.; Kwant, G.; Mook, G. A.; Zijlstra, W. G. Light absorbing properties, stability, and spectral stabilization of indocyanine green. J. Appl. Physiol. 1976, 40, 575-83).

Saxena V. et al. (Journal of Photochemistry and Photobiology B: Biology 74 (2004) 29-39) disclose poly(DL-lactic-co-glycolic acid) and polyvinyl alcohol polymeric nanoparticles for improving aqueous-stability, photo-stability and thermal stability to ICG. In this work, even if the stability of ICG loaded nanoparticles was improved due to the entrapment of ICG in the polymeric envelop (showing half-life in aqueous solution of 2.5-3 days), ICG in nanoparticles shows a decrease in its peak fluorescence intensity with respect to the free ICG solution. This finding together with high particle size distribution (mean diameter around 350 nm) could result in low efficiency in the in vivo imaging of tumor targeting.

WO2010/018216 discloses a fluorescent nanoemulsion of ICG Indocyanine green, comprising in the oily phase ICG, at least one amphiphilic lipid and at least one solubilising lipid which is solid at 25° C. According to this reference, the droplets in the nanoemulsion should have an amorphous core, because crystallinity is deemed detrimental to the stability of the nanoemulsion favouring the expulsion of the encapsulated molecules to the outside of the droplets or their aggregation.

In spite of the apparent progress provided by the above nanoparticles and nanoemulsion, ICG use in near-infrared imaging still encounters problems. Altinoglu and Adair (WIREs Nanomedicine and Nanobiotechnology, Volume 2, September/October 2010, 461-477) confirm superior optical and stability properties of Quantum Dots (QDs) in NIR imaging. However, toxicity problems hinder their use and NIR dyes are still proposed. Encapsulation of ICG in nanoparticles synthesized from calcium phosphate is reviewed and in spite of the lower performance with respect to QDs, their clinical application is proposed.

Zheng et al. (Mol. Pharmaceutics 2011, 8, 447-456), in order to overcome the problems of poor aqueous stability of ICG, its nonspecific binding to proteins and lack of target specificity, disclose an ICG-containing nanostructure exploiting the non-covalent self-assembly chemistry between phospholipid-polyethylene glycol (PL-PEG) and ICG. The dual functionality of this nanostructure for targeted optical imaging and photothermal therapy is proposed. Their use in in vivo photothermal therapy has been recently described (Zheng et al. Mol. Pharm, 2012, 9(3):514-522).

Navarro et al. (Journal of Biomedical Nanotechnology, Vol. 8, 594-604 and 730-741, 2012) disclose lipid nanoparticle vectorization (LNP) of ICG as beneficial for intraoperative fluorescence. In the work, it is quantified for up to two days the improvement on in vivo tumor/skin and ex vivo tumor/muscle fluorescence ratio of the ICG-LNP in comparison to the free dye injection (by a factor of 2 between 24 and 48 h).

US2006/0083781 discloses solid lipid nanoparticles which are functionalized in view of their use in tumor targeting therapeutic systems, thermoresponsive payload delivery systems, magnetic-driven targeting systems, therapeutic diagnostic systems, stabilized ink compositions and cosmetic formulations. Furthermore, the developed process is amenable to encapsulation of the quantum dots in a lipid environment diminishing their accessibility to oxidative species and Cd-associated toxicity.

A review of the state of the art dealing with all methods for solid lipid nanoparticles preparation is provided in Sawant and Dodiya (Recent Patents on Drug Delivery & Formulation 2008, 2, 120-135). In order to optimize the delivery properties of a nanoparticle a particle size lower than 100 nm is preferably required. On the contrary, many of the methods exploited in the literature provide SLNs with an average particle size in the micrometer range (Cortesi et al., Biomaterials 2002; 23:2283-2294) or not lower than 200 nm (Garcia-Fuentes et al. Colloids and Surfaces B: Biointerfaces, 2003, 27: 159-168; Morel et al. European Journal of Pharmaceutics and Biopharmaceutics 45 (1998) 157-163), i.e. well above the preferred nano-size range.

Advantageously, in the present invention the formulation of nanosuspensions shows particle size lower than 100 nm and shows a prolonged blood circulation half-life and an improved photostability and fluorescence signal.

These unexpected results were achieved by the optimization of the amphiphilic components and the preparation method.

SUMMARY OF THE INVENTION

It has now unexpectedly been found that incorporating ICG as well as other fluorescent dyes analogues of ICG together with other chemical structures into solid lipid nanoparticles, the above problems of the prior art have been solved, also providing further advantages, as it will be apparent from the following disclosure of the invention.

It is an object of the present invention a solid lipid nanoparticle (hereinafter also referred to as SLN or simply nanoparticle) comprising:
a. a solid lipid core comprising at least a glyceride and/or at least a fatty acid;
b. a mixture of amphiphilic components;
c. an amphiphilic component consisting in an alkaline-earth complex with a compound of formula I and/or II:

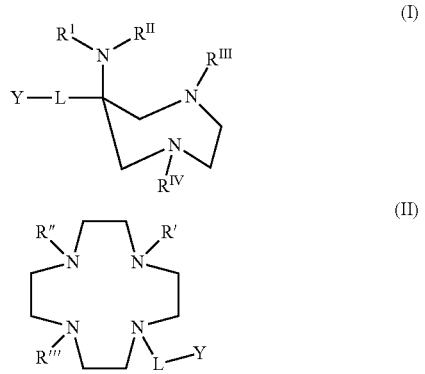

wherein the groups will be defined in the following description.
d. a fluorescent dye of the cyanine family and/or a polyetherocyclic compound including coumarin, pyrano, quinoline, pyranoquinoline, indole and pyranoindole derivates in acid form or a pharmaceutically acceptable salt thereof.

It is another object of the present invention a process for the preparation of said nanoparticles.

It is another object of the present invention a pharmaceutical composition comprising the above-mentioned nanoparticles, in particular for use in diagnostics.

It is another object of the present invention the above-mentioned nanoparticles for use as diagnostic agents.

Another object of the present invention is the above nanoparticle wherein a molecular targeting moiety is present on the nanoparticle surface achieving relevant binding affinity towards a selected target organ, tissue or cell.

Another object of the present invention is the above nanoparticle for use as diagnostic agent in instrumental diagnostics, in particular real-time imaging-guided surgery.

Another object of the present invention is the above nanoparticle for use as diagnostic agent in tumor detection and lymph nodes mapping in clinical fluorescence imaging applications, in particular in real-time visualization of cancerous lesions and sentinel lymph node detection during surgery lesions removal or endoscopic/laparoscopic surgical treatments.

The SLN of the present invention, when loaded with the fluorescent dye, allows a prolonged blood circulation half-life with subsequent accumulation in the pathological tissues of interest by the enhanced permeability and retention (EPR) effect.

The SLN according to the present invention shows enhanced photostability due to the lipidic matrix protection effect and improved fluorescence signal with respect to the free form of the fluorophore.

Furthermore, the lipidic components can preserve the dye from degradation factors depending on the interaction with quenchers molecules or from chemical degradation due to critical biological conditions (i.e. acidic pH) or from light exposure (photobleaching processes).

Finally, the formulation of the fluorescent dye into the SLN according to the present invention improves the fluorescent quantum yield ($\Phi$) of the dye due to the decrease of the non-radiative relaxation rate resulting from the steric constraints of the surrounding components.

These and other objects and advantages will be disclosed in detail in the following description also by means of figures and examples.

Figure 4A:
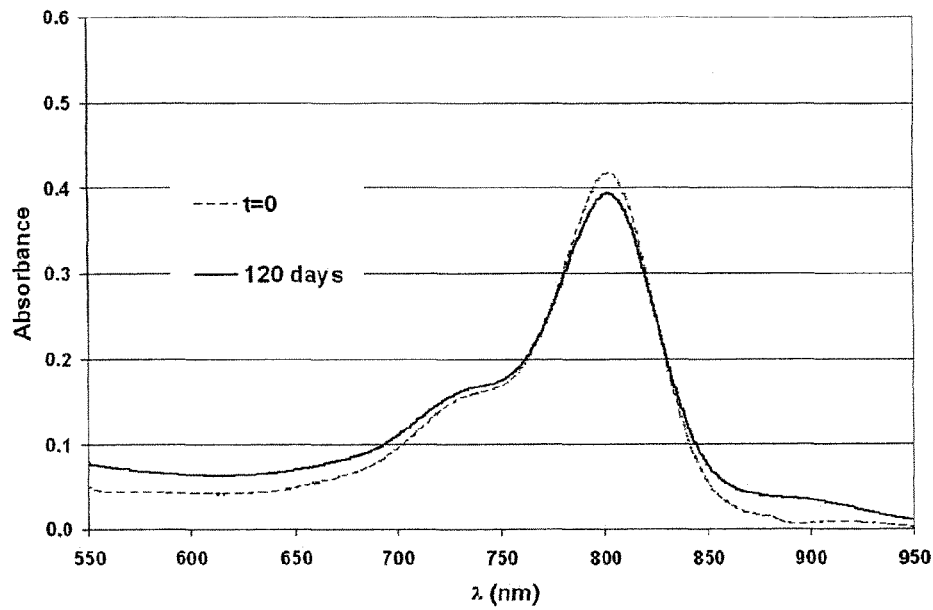
Figure 4B:
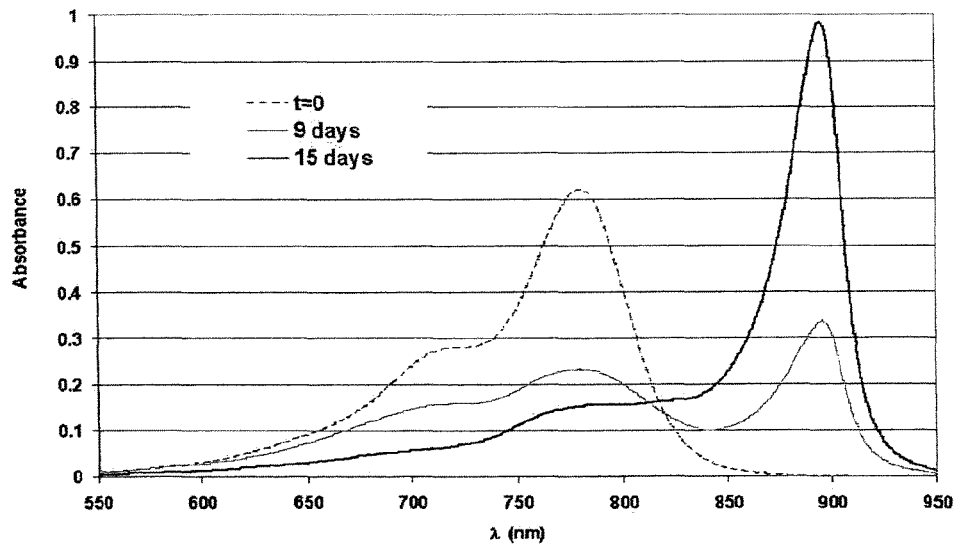

FIG. 4. panel A represents the UV-Vis spectra of ICG loaded SLNs in aqueous solution at time zero (dashed line) and after 120 days from formulation (black line); panel B shows a UV-Vis spectra of ICG in aqueous solution at different time points (time 0: dashed line; 9 days: grey line; 15 days: black line).

Figure 5:
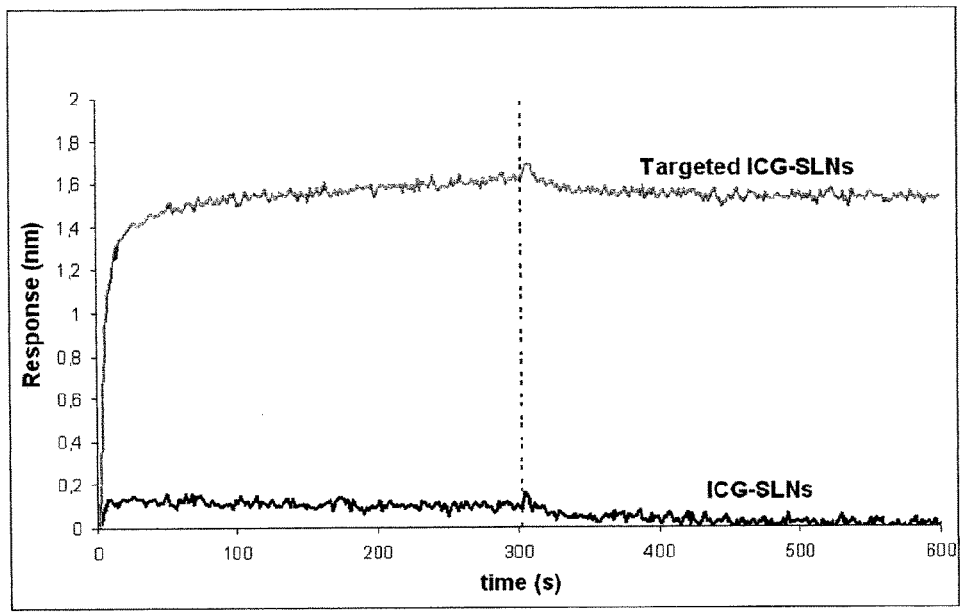

FIG. 5 represents laser Interferometry experiments for the evaluation of the binding affinity towards anti-folic acid IgG of: FA-ICG loaded SLN (Targeted ICG-SLNs) and non targeted SLN (ICG-SLNs).

Figure 6:
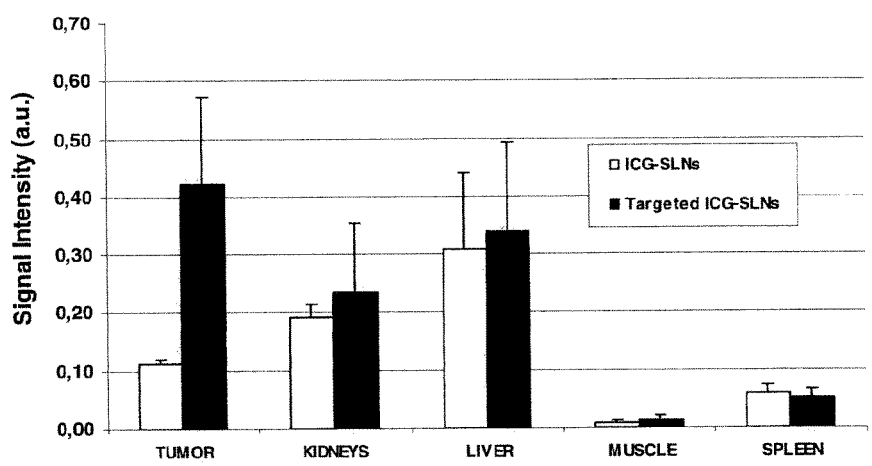

FIG. 6 represents ex-vivo analysis of mice (n=6) at 24 h after administration of ICG loaded SLNs and FA-ICG loaded SLNs in IGROV-1 xenograft ovarian carcinoma bearing Balb/C nu/nu mice.

Figure 7A:
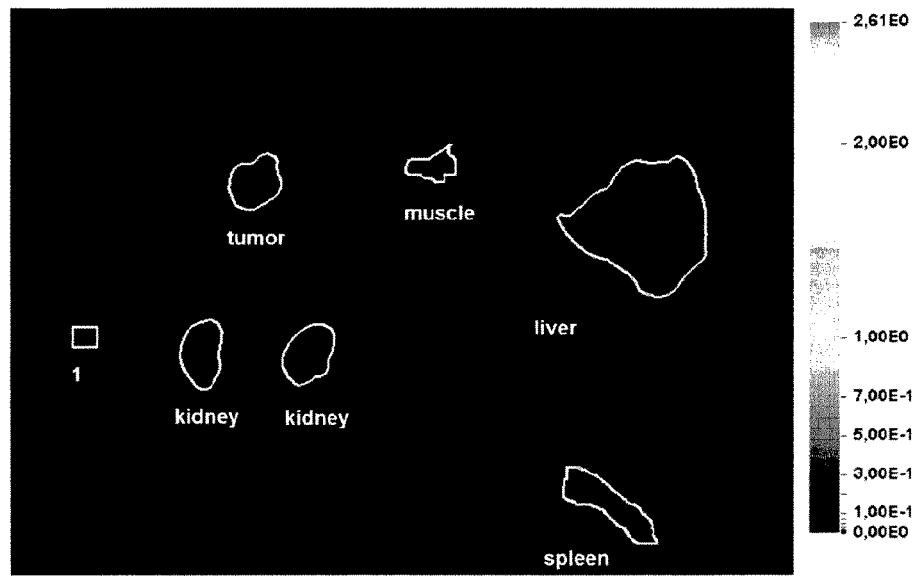
Figure 7B:
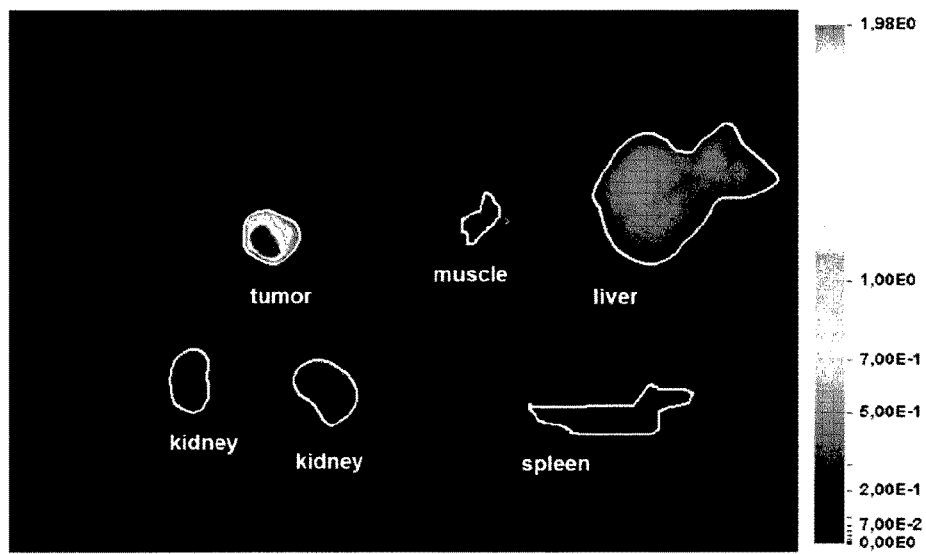

FIG. 7 represents ex-vivo analysis of two representative mice at 24 h after administration of ICG-SLNs (panel A) and FA-ICG-SLNs (panel B) in IGROV-1 xenograft ovarian carcinoma bearing Balb/C nu/nu mice.

Figure 8:
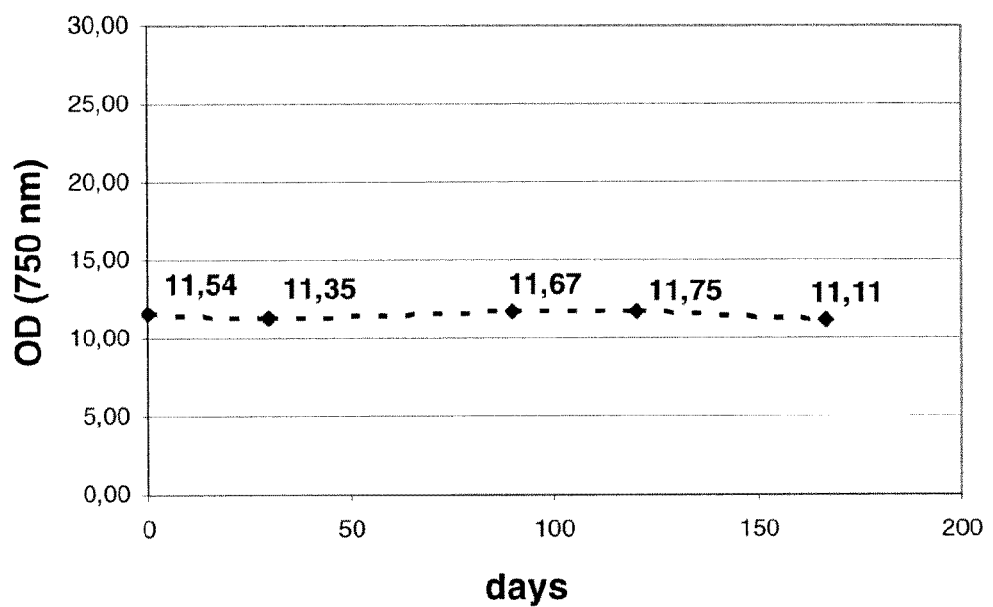

FIG. 8 represents optical density (750 nm) of a targeted ICG-loaded SLNs

Figure 9:
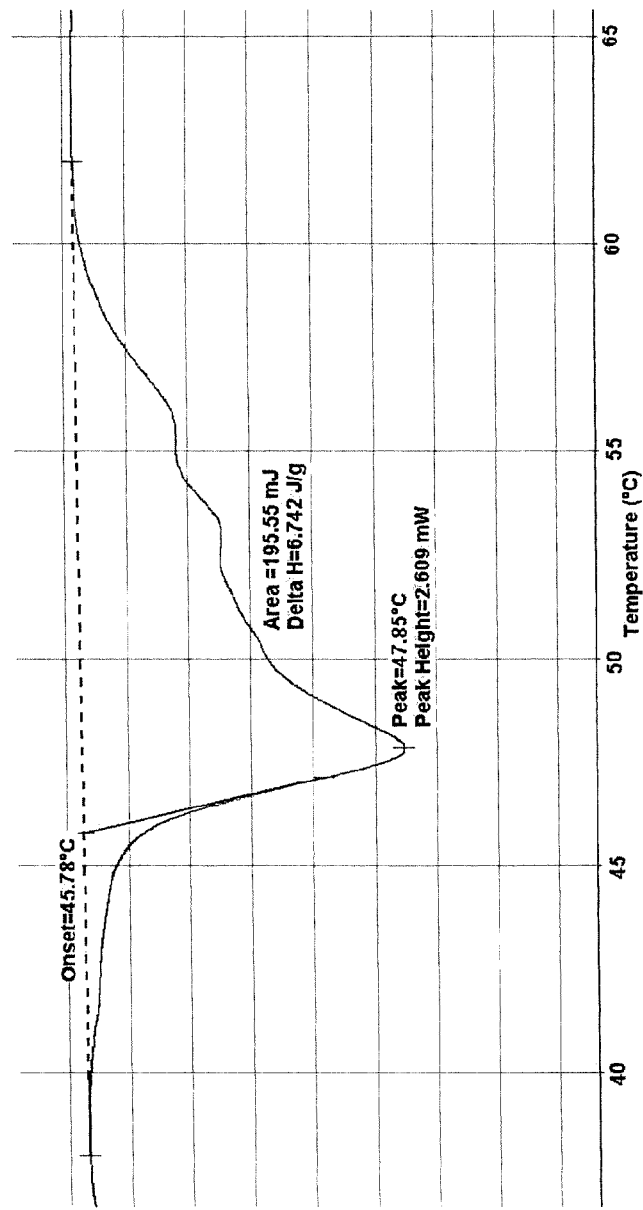

FIG. 9 represents a DSC of ICG-loaded SLNs of example 1.

Figure 10:
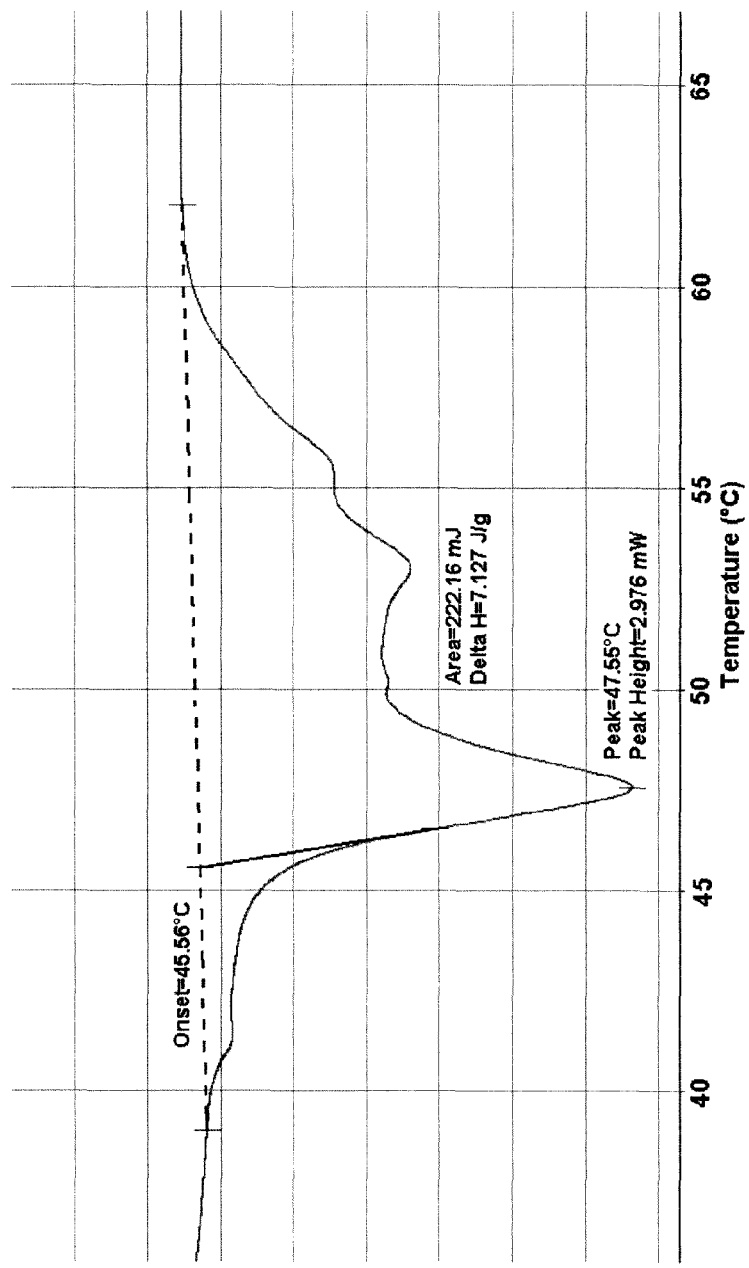

FIG. 10 shows the DSC curve of the ICG-loaded SLNs of example 2.

DETAILED DISCLOSURE OF THE INVENTION

The nanoparticle according to the present invention comprises as essential components:

a) a solid lipid core comprising at least a glyceride and/or at least a fatty acid;

b) a mixture of amphiphilic components forming a shell around said core a);

c) an amphiphilic component consisting in an alkaline-earth complex with a compound of formula I and/or II:

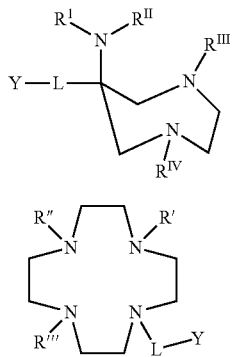

wherein the groups are defined below, or pharmaceutically acceptable salts thereof;
d) a fluorescent dye of the cyanine family and/or a polyetherocyclic compound including coumarin, pyrano, quinoline, pyranoquinoline, indole and pyranoindole derivates in acid form or a pharmaceutically acceptable salt thereof.

In another embodiment of the present invention, said nanoparticle further comprises:
e) a hydrophilic polymer covalently linked to said shell b) having the function of stealth agent.

In another embodiment of the present invention, said nanoparticle further comprises:
f) a molecular targeting moiety for the specific binding towards one pathology-related biological marker, said moiety being linked either to said shell b) or said hydrophilic polymer e).

The following percent composition are related to the amount of the components from a) to f) used for the preparation of SLNs without considering the contribution of ionic surfactants and low molecular weight alcohols whose the final suspension is substantially free.

In the following, each component a) to f) is expressed as weight/weight % with respect to the total weighted amount of the SLNs dry component.

The solid lipid core a) comprises at least one glyceride, preferably a triglyceride and/or at least one fatty acid or an ester thereof, or a mixture thereof which is or are in the solid form at least in the temperature range comprised from room temperature (i.e. about 20-25° C.) to body temperature (37° C.). In a first embodiment of the present invention, said solid lipid core a) comprises at least a glyceride selected from the group consisting of a monoglyceride, a diglyceride or a triglyceride, having a saturated or unsaturated, linear or branched $C_{12}$-$C_{24}$ acyl chain. In case of di- and triglyceride, the acyl chains can be the same or different. Said fatty acid or an ester thereof, has a saturated or unsaturated, linear or branched $C_{12}$-$C_{24}$ carbon chain. Esters of said fatty acids are also provided to the purpose of the present invention, preferably esters with $C_{12}$-$C_{24}$ fatty alcohols are provided.

For the purposes of the present invention, as "solid lipid core" it is intended a lipid core which is solid at a temperature comprised between room temperature (i.e. about 20-25° C.) and body temperature (i.e. about 37° C.).

The solid core, herein also referred as the "lipid component", which may constitute about 30-50% (weight/weight), preferably 35-45%, comprises at least one glyceride selected from the group consisting of: monoglycerides, diglycerides or triglycerides with saturated or unsaturated, linear or branched hydrocarbon chains with length ranging from 12-24 carbon atoms, with melting temperatures greater than 37° C., or mixtures thereof, and/or a at least one saturated or unsaturated, linear or branched $C_{12}$-$C_{24}$ fatty acid, or an ester thereof provided that the selected ratio provides a solid composition in the above indicated conditions.

The lipid component may also be a mixture of mono, di- or tri-glycerides such as for example the commercial mixtures known under the name of SOFTISAN® and Witepsol® preferably Witepsol® W35, H42, E76, E85 or SOFTISAN® 138, 142, 154.

Preferably the lipid component consists of triglycerides such as glyceryl tripalmitate, glyceryl distearate, glyceryl tristearate, glyceryl trimyristate, glyceryl trilaurate, glyceryl triarachidate or a mixtures thereof. According to a particularly preferred embodiment, the solid core comprises glyceryl tripalmitate (tripalmitin).

The lipid component preferably comprises at least a $C_{12}$-$C_{24}$ fatty acid, whose hydrocarbon chain can be saturated or unsaturated, linear or branched. Preferably the fatty acid is selected from: myristic acid, palmitic acid, stearic acid, behenic acid or mixtures thereof. Said core optionally comprises mono- or diesters $C_{12}$-$C_{24}$ fatty acids with $C_{12}$-$C_{24}$ fatty alcohols. The fatty acid ester component can be further represented, for example, by cetylpalmitate.

A preferred lipid combination is tripalmitin and stearic acid.

According to an alternative embodiment, the lipid component in a) may comprise other lipids insoluble in water but soluble in organic solvents. For example, the lipid can be esterified poly(acrylic acid) or esterified poly(vinyl alcohol). In particular, the lipid can be poly(acrylic acid) wholly or partially esterified with one or more alcohols. In one aspect, less than all of the acrylic acid residues are esterified. In a further aspect, substantially all of the acrylic acid residues are esterified. The polymer can be a homopolymer or a copolymer. In one aspect, the lipid can comprise at least one $C_4$-$C_{24}$ alcohol. In one aspect, the alcohol can be saturated or unsaturated, can be linear or branched, and can be substituted or unsubstituted. The alcohols at each acrylic acid residue can be the same or can be different. In another embodiment, the lipid can be poly(vinyl alcohol) wholly or partially esterified with one or more carboxylic acids. In one aspect, less than all or substantially of the vinyl alcohol residues are esterified. The polymer can be a homopolymer or a copolymer. The carboxylic acid at each vinyl alcohol residue can be the same or different.

In SLNs the lipid component is solid and in amorphous or crystalline form.

According to a particularly preferred embodiment, the solid core comprises tripalmitin and stearic acid and is crystalline.

As to the component b), the invention comprises the use of an amphiphilic compound as surfactant component. The surfactant component is selected from the group consisting of phospholipids, lysolipids and sphingolipids having linear or branched, saturated or unsaturated $C_6$-$C_{24}$ hydrocarbon chains; optionally at least one of cholesterol and steroid derivatives, glycolipids, fatty acids, fatty alcohols and dialkyl ethers, non-ionic surfactant such as sorbitan derivatives, preferably polyoxyethylen monooleate or monopalmitate derivatives (such as Polysorbate 20 known with the commercial brand names Alkest TW 20®, Tween 80®), di- and tri-esters of saturated and unsaturated fatty acid derivatives from $C_6$-$C_{24}$ carbon atoms and ethoxylated analogue thereof; mono or oligo-glycosides and ethoxylated analogues thereof, glycerol mono, di- and tri-esters liquid at room and at body temperature. The surfactant component represents 25-60% (weight/weight) of the SLN. Preferably about 27-45% and more preferably 30-38% of SLNs composition comprises phospholipids;

In this regard, examples of phospholipids are dilauroylphosphatidylcholine (DLPC), dimyristoylphosphatidylcholine (DMPC), dipalmitoylphosphatidylcholine (DPPC), diarachidoylphosphatidylcholine (DAPC), distearoylphosphatidylcholine (DSPC), dioleoylphosphatidylcholine (DOPC), 1,2-distearoyl-sn-glycero-3-ethylphosphocholine (Ethyl-DSPC), dipentadecanoylphosphatidylcholine (DPDPC), 1-myristoyl-2-palmitoylphosphatidylcholine (MPPC), 1-palmitoyl-2-myristoylphosphatidylcholine (PMPC), 1-palmitoyl-2-stearoylphosphatidylcholine (PSPC), 1-stearoyl-2-palmitoylphosphatidylcholine (SPPC), 1-palmitoyl-2-oleylphosphatidylcholine (POPC), 1-oleyl-2-palmitoylphosphatidylcholine (OPPC), dilauroylphosphatidylglycerol (DL-PG) and its alkali metal salts, diarachidoylphosphatidylglycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoylphosphatidylglycerol (DOPG) and its alkali metal salts, dimyristoylphosphatidic acid (DMPA) and its alkali metal salts, dipalmitoylphosphatidic acid (DPPA) and its alkali metal salts, distearoylphosphatidic acid (DSPA), diarachidoylphosphatidic acid (DAPA) and its alkali metal salts, dimyristoylphosphatidylethanolamine (DMPE), dipalmitoylphosphatidylethanolamine (DPPE), distearoylphosphatidylethanolamine (DSPE), dioleylphosphatidylethanolamine (DOPE), diarachidoylphosphatidylethanolamine (DAPE), dilinoleylphosphatidylethanolamine (DLPE), dimyristoylphosphatidylserine (DMPS), diarachidoylphosphatidylserine (DAPS), dipalmitoylphosphatidylserine (DPPS), distearoylphosphatidylserine (DSPS), dioleoylphosphatidylserine (DOPS), dipalmitoylsphingomyelin (DPSP), and distearoylsphingomyelin (DSSP), dilauroylphosphatidylinositol (DLPI), diarachidoylphosphatidylinositol (DAPI), dimyristoyl-phosphatidylinositol (DMPI), dipalmitoylphosphatidylinositol (DPPI), distearoylphosphatidylinositol (DSPI), dioleoylphosphatidylinositol (DOPI) or mixtures thereof.

In one embodiment of the present invention, the amphiphilic component b) includes phospholipids, preferably of natural origin. In a preferred embodiment, the component b) includes phosphatidylcholine from soy lecithin, commercially available as Epikuron 200®. Examples of other phospholipids of natural origin are Epikuron 170® or Epikuron 100®, Lipoid® S 75, Lipoid® S 100 or egg lecithin Lipoid® E80.

Amphiphilic components can also comprise bile acids or their salts, cholesterol and steroid derivatives as 6-(5-cholesten-3β-yloxy)-1-thio-β-D-galactopyranoside; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyrano-side, glycolipids, fatty acids, fatty alcohols and dialkyl ethers, said acids, esters and alcohols having a straight or branched $C_6$-$C_{24}$ carbon chain, tocopherol and tocopherol emisuccinate.

Other amphiphilic components can also include non-ionic surfactant, preferably sorbitan mono-, di- and tri-esters of saturated and unsaturated fatty acid derivatives having $C_6$-$C_{24}$ carbon atoms and ethoxylated analogues thereof. In a preferred embodiment, the composition includes polyoxyethylene sorbitan monooleate commercially available as Tween 80® and/or similar compounds such as Polysorbate 60 (Tween® 60), Polysorbate 40 (Tween® 40). Additional sorbitan derivatives such as Sorbitan monopalmitate (Span® 40) Sorbitan monostearate (Span® 60), sorbitan monooleate (Span® 80) may also be included. Preferably this component constitutes 5-20% and even more preferably constitutes about 8-12% of SLNs.

Other amphiphilic components can also include mono or oligo-glycosides and ethoxylated analogues thereof, glycerol mono, di- and tri-esters soluble at room and at body temperature. The feature of being soluble at room temperature and at body temperature is indicative of the chain length to the person skilled in this art.

The amphiphilic components also include a ionic surfactant. In a preferred embodiment, anionic surfactants, such as cholic acid, derivatives or salts thereof are preferred. Among cholic acids, particularly preferred are: taurocholic and taurodeoxycholic acids or their derivatives or salts, such as sodium cholate, sodium taurodeoxycholate and sodium taurocholate. In a more preferred embodiment taurocholic acid sodium salt hydrate is included in the formulation. Other anionic surfactants as polyalkylphophates, alkyl sulphonate and sulphate, alkyl sulfosuccinnate having from 6 to 24 carbon atoms can also be included.

Co-surfactant agents can be included in the formulation. In a preferred embodiment alcohols having $C_3$-$C_8$ hydrocarbon chain, preferably mono-alcohols, such as for example 1-propanol, 1-butanol, 1-pentanol, 1-hexanol, 1-heptanol and 1-octanol, 3-pentanol and 4-heptanol can be included. Most preferred are: 1-butanol and/or 1-hexanol.

According to the component c), the invention comprises the use of an amphiphilic compound as stabilizer agent. In particular, component c) allows the particle to maintain its size during time and contributes to the SLN particle stability, as better detailed in the Experimental Part. The amphiphilic compound is a complex of an alkaline earth metal selected from coordination compounds, characterized by a lipophilic aliphatic part and a coordination cage. Such coordination cage mainly belongs to two classes: diazepine derivatives (Formula I) and tetraazacyclododecane derivatives (Formula II).

Therefore, component c) is a compound of formula (I) or of formula (II):

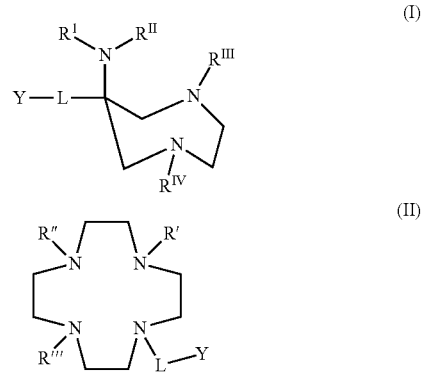

wherein:
Y is a group of formula Y'—NH— or (Y')$_2$—N—, wherein Y', which in case of (Y')$_2$—N can be the same or different, is selected from the group consisting of: linear or branched, saturated or unsaturated $C_{12}$-$C_{20}$ alkyl group; $C_1$-$C_{10}$ alkyl group, optionally interrupted by a phosphate group —O—(HO—P=O)—O—, or optionally substituted by one or more atoms or groups selected from the group consisting of: OH, COOR$_1$, oxycarbonyl(C$_{12}$-C$_{18}$)alkyl and oxycarbonyl-(C$_{12}$-C$_{18}$)alkenyl; wherein R$_1$ is selected from the group consisting of hydrogen H and a linear or branched C$_1$-C$_4$ alkyl group; or Y' is a monophosphate ester of a substituted or partially substituted glycerol, having at least one functional group of said glycerol esterified with an aliphatic fatty acid with saturated or unsaturated carbon chains, and the other two functions of phosphoric acid being either free or salified with alkali or earth alkali metals;

L is a bivalent linker selected from the group consisting of: aliphatic linear or branched C$_1$-C$_6$ alkanediyl, alkenediyl, alkynediyl, optionally interrupted with one or more atoms or atom groups selected from the group consisting of: —C=O, —C=S, —COO, —OCO, —CONR$_1$—, —O— and —S—, wherein R$_1$ is as defined above;

R$^{I-IV}$ are each, independently, an —R$_2$—COOR$_3$, wherein R$_2$ is a C$_1$-C$_6$ linear or branched alkyl, R$_3$ is H or a pharmaceutically acceptable cation.

R$^{I'-I''''}$ are each, independently, an —R$_2$—COOR$_3$, wherein R$_2$ is a C$_1$-C$_6$ linear or branched alkyl, R$_3$ is H or a pharmaceutically acceptable cation.

The Y group is linked to the L group preferably by means of an amide bond between a terminal nitrogen atom of the Y group and a carbonyl (—C=O) or thyocarbonyl (—C=S), present at the terminal end connecting with Y. Preferably, the Y group is in the form: (Y')$_2$—N—, wherein Y' residues are the same or different and are alkyl chains, have length C$_{12}$-C$_{20}$, preferably C$_{16}$-C$_{18}$. Alternatively, the Y group may also have the formula: Y'—NH—, wherein Y' is C$_{12}$-C$_{20}$ alkyl group, more preferably C$_{16}$-C$_{18}$ alkyl group, interrupted by one or more phosphate groups of formula:

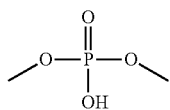

According to this embodiment, Y is a phospholipid having the formula: Y'—NH— wherein Y' is a C$_{16}$-C$_{18}$ alkyl group, interrupted by one or more groups of formula:

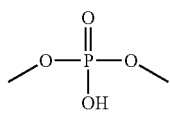

further substituted with at least one and preferably 2 or 3 carboxyalkyl groups containing 12-20 carbon atoms, or more preferably 16-18 carbon atoms.

In a further alternative embodiment, Y' is a monophosphate ester of a substituted or partially substituted glycerol, having at least one functional group of said glycerol esterified with an aliphatic fatty acid with saturated or unsaturated carbon chains, and the other two functions of phosphoric acid being either free or salified with alkali or earth alkali metals. Preferably, a fatty acid is a C$_{14}$-C$_{20}$ carboxylic acid.

Therefore, according to a preferred embodiment of Y', the same or different when (Y')$_2$—N—, is selected from the group consisting of:
linear or branched, saturated or unsaturated C$_{16}$-C$_{18}$ alkyl group;

C$_4$-C$_6$ alkyl group interrupted by a phosphate group —O—(HO—P=O)—O— and/or optionally substituted by one or more atoms or groups selected from the group consisting of: oxycarbonyl-(C$_{12}$-C$_{18}$)alkyl and oxycarbonyl-(C$_{12}$-C$_{18}$)alkenyl;

or Y' is a monophosphate ester of a substituted or partially substituted glycerol, having at least one functional group of said glycerol esterified with an aliphatic fatty acid wherein said aliphatic fatty acid is a C$_{14}$-C$_{20}$ carboxylic acid with saturated or unsaturated carbon chains, and the other two functions of phosphoric acid being either free or salified with alkali or earth alkali metals; being L, R$^{I-IV}$ and R$^{I'-I''''}$ as defined above.

Even more preferably, when Y' is a C$_4$-C$_6$ alkyl group interrupted by a phosphate group —O—(HO—P=O)—O—, it is preferably further substituted by at least two atoms or groups selected from the group consisting of: oxycarbonyl-(C$_{14}$-C$_{16}$)alkyl and oxycarbonyl-(C$_{14}$-C$_{16}$)alkenyl. According to this further alternative embodiment, Y is selected from the following groups:

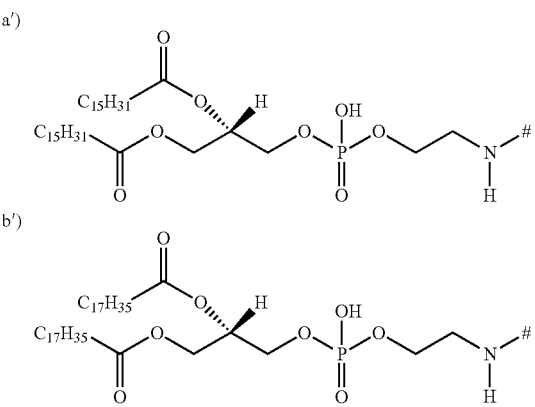

wherein # indicates the point of attachment to the linker L.

The linker L is a bivalent group which in the derivatives of formula (I) connects the diazepine moiety to the Y group and, similarly, in the derivatives of formula (II) connects the tetraazacyclododecane to the Y group.

Preferably, L is a linear or branched C$_1$-C$_6$ alkyl, alkenyl or alkynyl group, functionalized at one terminal side with a thiocarbonyl group (—C=S), or more preferably with a carbonyl group (—C=O) as a point of attachment for the terminal nitrogen atom of the Y residue in the formula (I) and (II).

Examples of linker L are: methylcarbonyl, ethylcarbonyl, propylcarbonyl, butylcarbonyl, pentylcarbonyl and hexylcarbonyl.

For the compounds of formula (I), more preferably the linker L is selected from: butyl-carbonyl of formula c'):

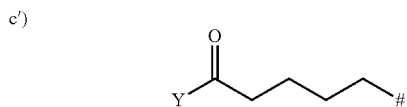

wherein # indicates the point of attachment to a diazepine of formula (I).

For the compounds of formula (II), the linker L is preferably selected from: methyl carbonyl of formula d') and carboxypropylcarbonyl of formula e').

d')

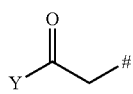

e')

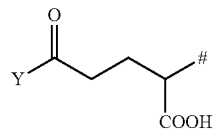

wherein # indicates the point of attachment to tetraazacyclododecane of formula (II).

As indicated above, the linker L is attached on one end to the Y group and on the other end to the diazepine or tetraazacyclododecane. The Y group of formula Y'—NH— or (Y')$_2$—N— has a terminal nitrogen atom to which the linker L is attached through an amide bond.

For compounds of formula (I), preferably L-Y-systems are selected from:

f')

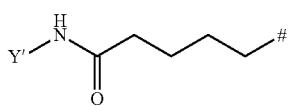

g')

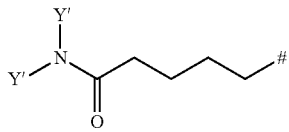

wherein Y' is in agreement with the above definitions and # indicates the point of attachment to diazepine of the derivative of formula (I).

For the compounds of formula (II), L-Y-systems are preferably selected from:

h')

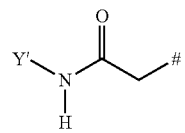

i')

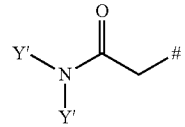

l')

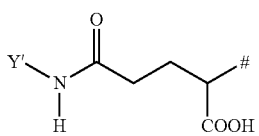

m')

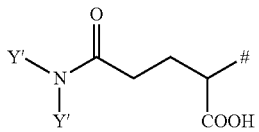

wherein Y' is defined as above and # indicates the point of attachment to tetraazacyclododecane of the derivative of formula (II).

According to a preferred embodiment, the compounds of formula (I) are selected from the group consisting of:

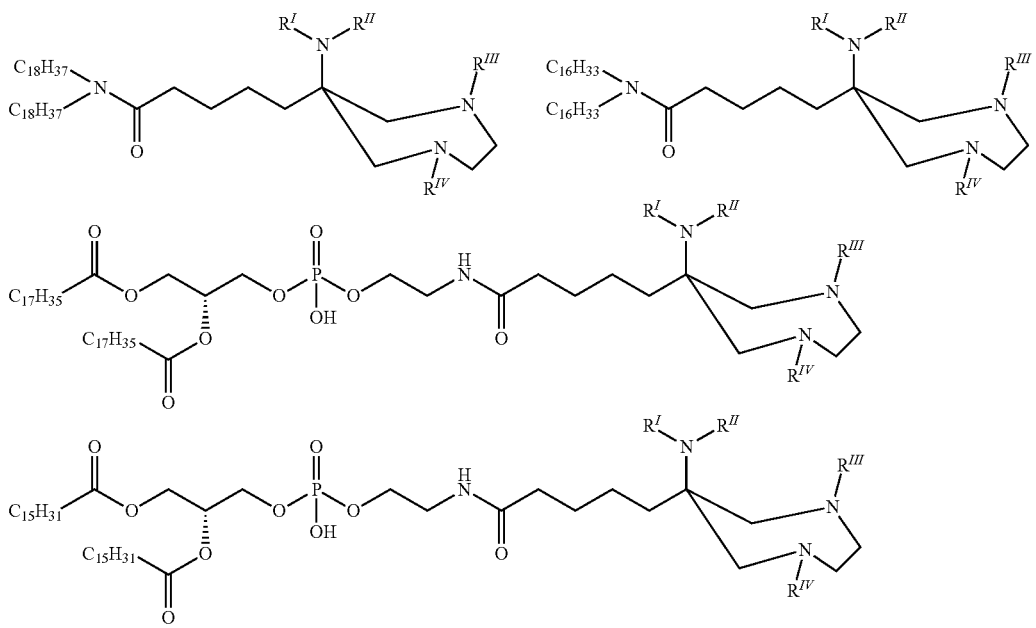

wherein $R^{I-IV}$ are as herein defined.

According to a preferred embodiment, the groups $R^{I-IV}$ are identical and are preferably carboxymethyl groups selected from: $—CH_2—COOH$ and $—R_2—COO^-M^+$, wherein $R_2$ is as above defined and $M^+$ is a metal selected from the group consisting of $Mg^{2+}$, $Ca^{2+}$ and $Sr^{2+}$.

Consequently, chelating agents of formula (I) are preferably defined by the general formula (I'):

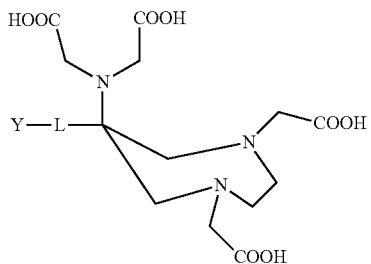
(I')

or a pharmaceutically acceptable salt thereof in the form of complex with an alkaline-earth metal, preferably $Ca^{2+}$, wherein L and Y and their combination of L-Y are as in the preferred embodiments described above.

Similarly and preferably, the chelating agents of formula (II), or pharmaceutically acceptable salts thereof have general formula (II'):

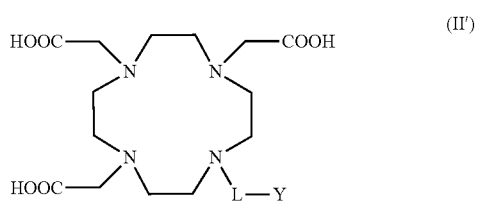
(II')

wherein L and Y, and their combination L-Y, are as in their preferred embodiments described above.

Therefore, in agreement with the structure of Y and L, the preferred compounds of formula (I') as a complex with an alkaline-earth metal, such as $Ca^{2+}$, $Sr^{2+}$, $Mg^{2+}$, preferably $Ca^{2+}$, or in the form of a pharmaceutically acceptable salt, are selected from the group consisting of:

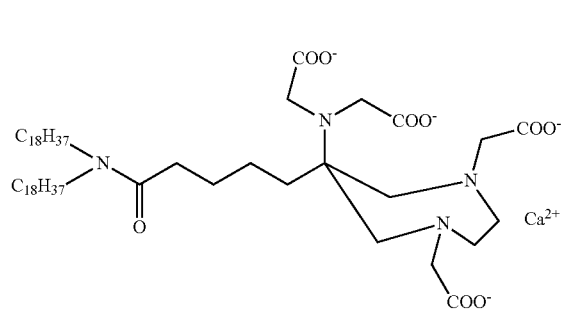
c.1

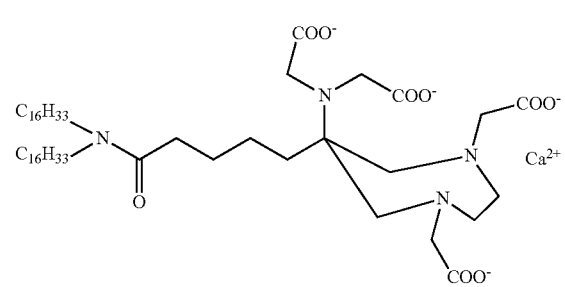
c.2

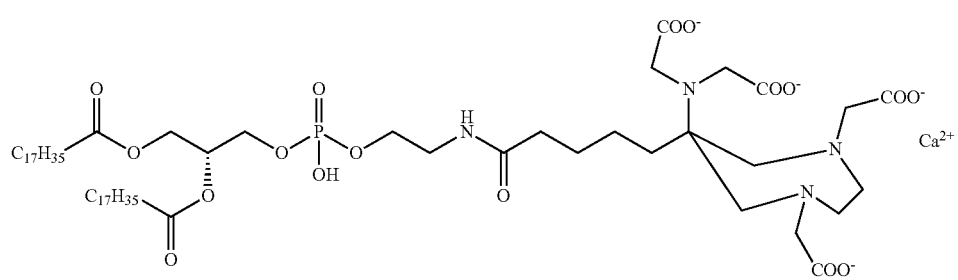
c.3

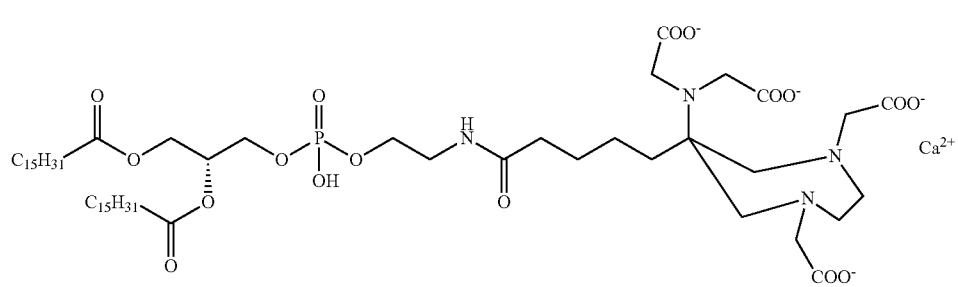
c.4

Preferred complexes of Formula (II') are selected from the group consisting of:

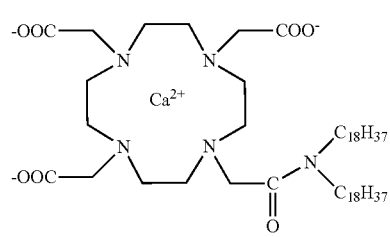

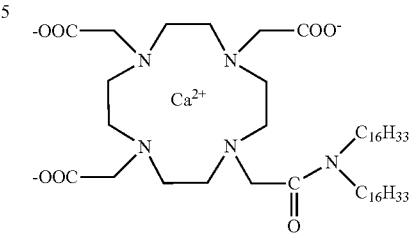

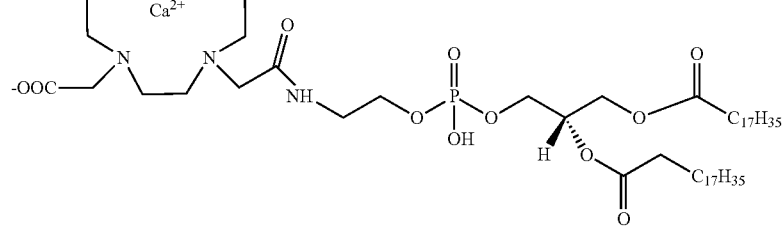

Particularly preferred are the complexes and salts thereof, selected from the group consisting of:
c.1: [6-[[Bis(carboxymethyl)]amino]-6-[5-(dioctadecylamino)-5-oxopent-1-yl]-tetrahydro-1H-1,4-diazepine-1,4(5H)-diacetate(4-)]calciate (2-);
c.4: [6-[[Bis(carboxymethyl)]amino]-6-[(13R)-10-hydroxy-10-oxido-5,16-dioxo-13-(1-oxohexadecyl)oxy]-9,11,15-trioxa-6-aza-10-phosphahentriacont-1-yl]-tetrahydro-1H-1,4-diazepine-1,4(5H)-diacetate(4-)]calciate (2-);
c.5: [10-[2-(dioctadecylamino)-2-oxoethyl]-1,4,7,10-tetraazacyclododecane-1,4,7-triacetate(3-)]calciate(1-);
c.7: [10-[(10R)-7-hydroxy-7-oxido-2,13-dioxo-10-[(1-oxooctadecyl)oxy]-6,8,12-trioxa-3-aza-7-phosphatriacont-1-yl]-1,4,7,10-tetraazacyclododecane-1,4,7-triacetate(3-)]calciate(1-); the most preferred being the complex c.5 and salts thereof, preferably a $Ca^{2+}$ salt:

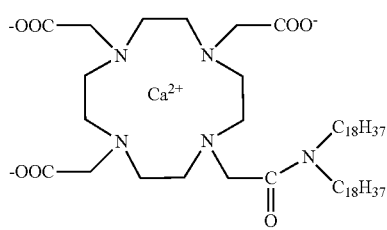

which is obtained by Ca complexation of the chelating agent 14 synthesized according to a procedure detailed in the Experimental Part, preparation 3.2.

Preferably, the stabilizing complex c) represents 4-13%, preferably 8-10% w/w of the total weight.

Synthesis of the Compounds of Formula I and II. General Scheme

The compounds of formula (I) of the present invention can be prepared by a process comprising at first the formation of an adduct between the selected linker L and the diazepine moiety, followed by activation of the carboxylic function on the terminal side of the linker, and subsequent amidation with the selected Y group. Finally, the protecting groups, where present in the obtained product, are removed and the derivative is optionally complexed with a selected alkaline-earth metal.

The adduct between the linker L and the diazepine moiety referred as "reagent" of the synthetic process is obtained by reaction of a suitable nitro derivative, which is a precursor of the selected linker, with N,N'-dibenzylethylenediamine, which is the precursor of the diazepine. Subsequently the nitro group is reduced and functionalized, typically by hydrogenation and subsequent N-alkylation under basic conditions. Said adduct between the linker and the diazepine moiety can advantageously be prepared and used as building block for the preparation of a series of derivatives of formula (I) by varying the selected moiety Y.

Therefore, the synthesis for the preparation of a compound defined by formulas (I) and (II) comprises the following steps:

a) preparation of an adduct of formula:

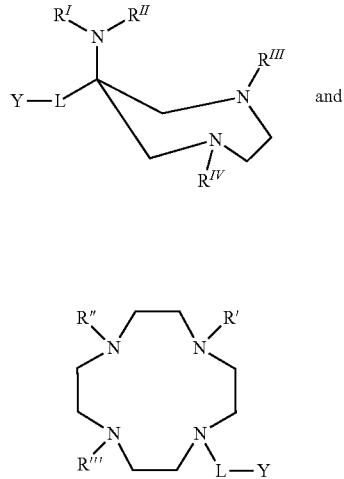
(I)

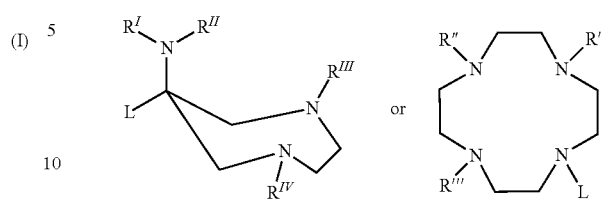

wherein $R^{I-IV}$ and $R'^{-'''}$ are as above defined and L is the linker comprising a terminal carboxylic function, b) activation of said terminal carboxylic function of the linker c) amidation reaction between the product of step b) and the Y group as above defined.

d) cleavage of any protecting group to give the derivative of formula (I) or (II);

e) chelation with an alkali-earth metal ion, to give the derivative of formula (I) or (II) in the form of a metal complex.

According to an illustrative example of the preparation of formula I compounds (to compound III in scheme 1), the process comprises, starting from a compound 5 as the starting adduct, the following steps b) to e):

Scheme 1

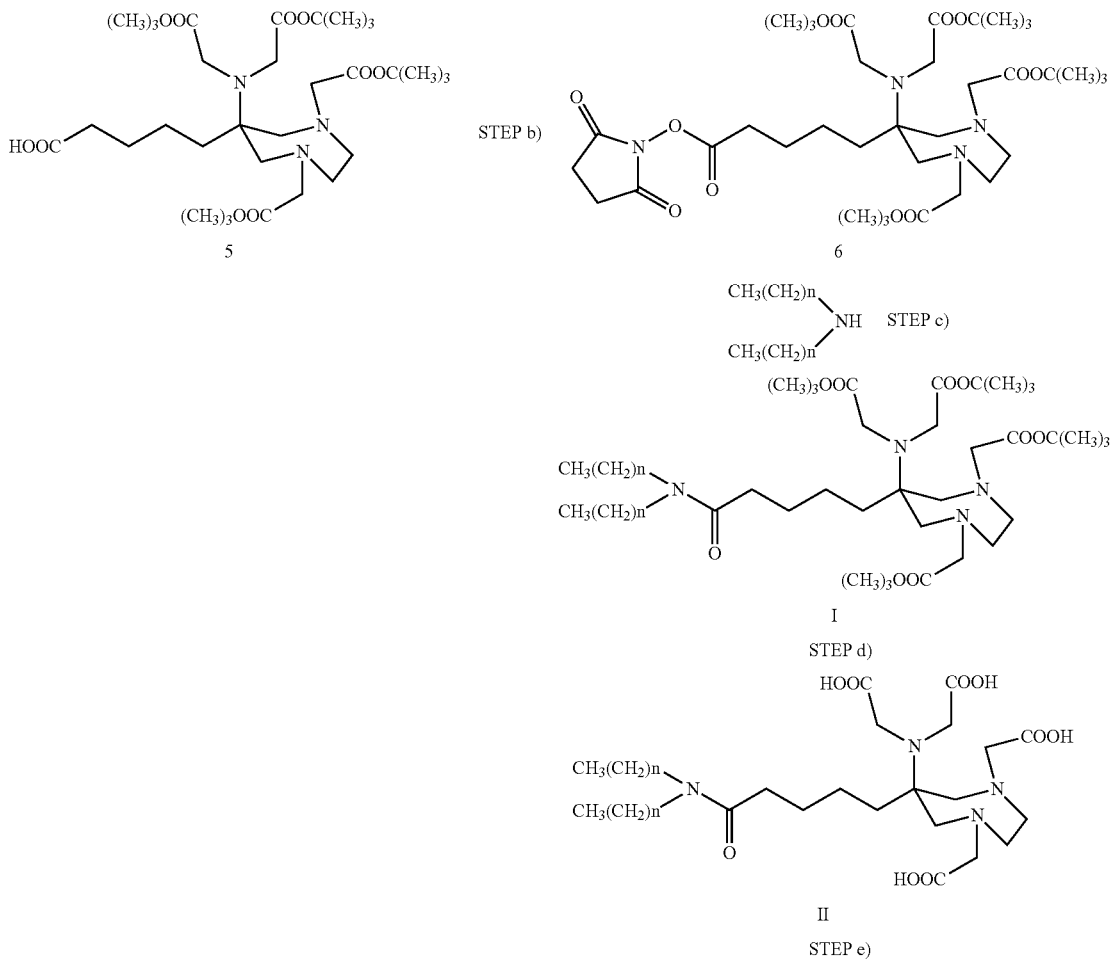

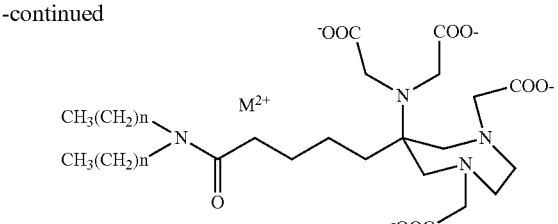

III

Adduct 5 between the linker and the diazepine moiety is prepared by reaction of N,N'-dibenzyethylenediamine diacetate and an alcoholic solution of 6-nitrohexanoic acid methyl ester 1, in the presence of paraformaldehyde followed by: reduction of the nitro group 2, functionalization of the amino derivative 3 and selective cleavage of the terminal carboxylic group 4, as indicated in Scheme 2, herein below:

Scheme 2

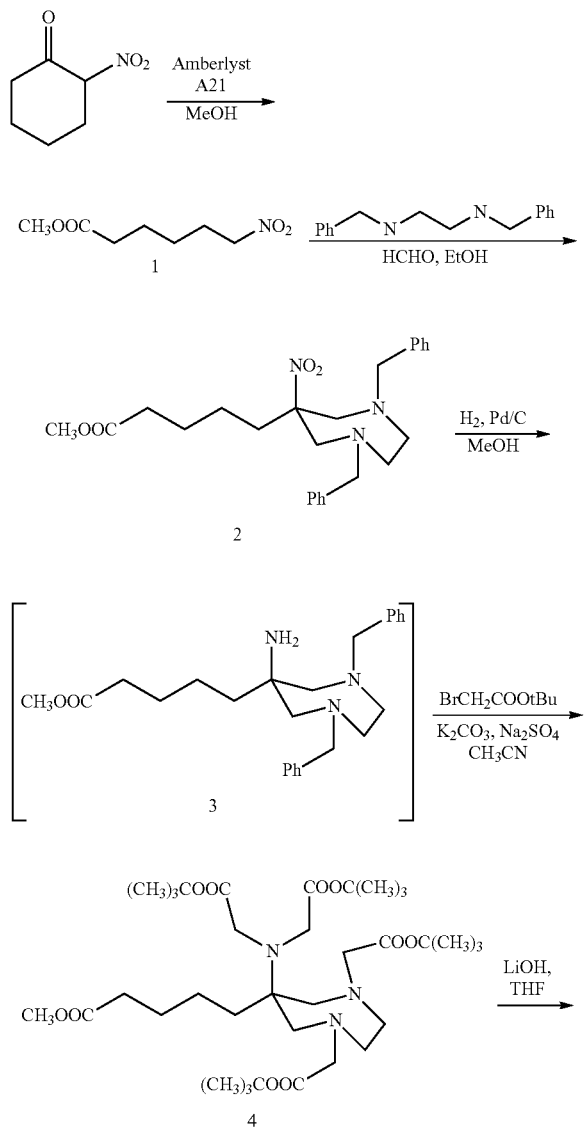

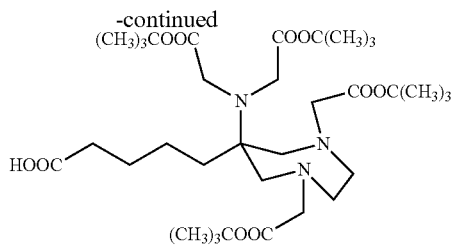

5

The diazepine derivative, as generally represented by compound 5, is subjected to the activation of the terminal carboxylic function as per step b) of the present process. The activation can be carried out according to procedures generally known in organic chemistry for the activation of carboxylic functions, typically by reaction with a carboxyl activating agent, such as N-hydroxysuccinimide (NHS) in the presence of a carbodiimide such as dicyclohexylcarbodiimide (DCC) or 1-ethyl-3-(3-dimethylaminopropyl)carbodiimide (EDC), in a molar ratio of at least 1:1 or preferably in a slight excess with respect to the starting material, e.g. in a molar ratio up to 1:1.5, in a proper organic solvent, such as an apolar organic solvent selected from: $CHCl_3$, $CH_2Cl_2$ and the like. Preferably, step b) is conducted in the presence of N-hydroxysuccinimide (NHS) and EDC in a molar ratio from 1:1 to 1:1.1 with respect to the starting material, and in the presence of $CH_2Cl_2$. The so-obtained derivative is then subjected according to step c) to an amidation reaction between the activated carboxylic terminal group of the linker L and the nitrogen atom of the selected Y residue for instance dialkyalmine, generally in the presence of a diisopropylethylamine (DIPEA). Preferably, the amidation reaction is carried out by dissolving the activated compound obtained after step b) in $CHCl_3$ and adding for instance dialkylamine and DIPEA in this order in a molar ratio from 1:1 to 1:1.7 with respect to the starting material. The solution is then stirred for a proper frame of time at a selected temperature, typically at room temperature (e.g. at a temperature comprised from 15 to 30° C.) generally for a period up to 20-24 hours. The thus formed amide product is then purified, e.g. by washing with water and by evaporating the separated organic phase, generally under vacuum or by distillation procedure. After purification, for instance by chromatography, the product of formula (I) is obtained in a protected form, e.g. preferably as tert-butyl ester derivative, in high yield (about 80%) and with a high degree of purity (about 95-99% HPLC).

According to step d) the derivatives of formula (I) obtained in their carboxylic protected form, can be readily deprotected under conditions known in the art, and dependent for instance on the kind of protecting group actually employed in step a). For a general reference on the choice of possible protecting groups, see "Greene's protective groups in organic synthesis" Wiley 14th Ed. In a preferred embodiment, the carboxylic function is protected as tert-butyl ester, and the deprotection is carried out under acidic conditions, typically in the presence of trifluoroacetic acid (TFA) and an organic apolar solvent such as $CH_2Cl_2$.

The synthesis of the compounds of formula (II) was carried out starting from commercially available 1,4,7,10-tetraazacyclododecane-1,4,7,10-tetraacetic acid tris(1,1-dimethyl)ethyl ester 11.

Compound 11 as defined in the experimental part have been subjected to activation of the carboxylic function, amidation reaction and deprotection of the protected carboxylic functions.

After deprotection, the so-obtained compounds of formula (I) and (II) can be suitably reacted with an alkaline-earth metal compound in order to obtain the corresponding metal complex derivatives. Said transformation is typically carried out by reaction with an inorganic or organic salt or oxide of the selected metal, operating in the presence of a solvent such as water or organic solvent, e.g. $CHCl_3$ MeOH or EtOH or mixture thereof. Preferred counter ions of the metal are chloride or acetate, and preferred salts are: $CaCl_2$, $Ca(OAc)_2$, whereas among preferred oxides: CaO.

The composition of the present invention can also contain at least one hydrophilic polymer e) with the function of stealth agent aimed at decreasing the recognition of the SLN comprising the fluorescent dye from the reticulo-endothelial system. In a preferred embodiment, the stealth agent is a hydrophilic polymer for the coating of the nanoparticle surface linked to a hydrophobic segment. The stealth agent can be a functionalized poloxamer, a polysiloxane, a polyalkyl polyether, polyglycerine, a polyvinilalcohol and a polyethyleneglycol, optionally covalently linked to a phospholipidic moiety. Mixtures of said components are also provided. Stealth agents are well-known in the art and they are suitable for use in the present invention. For example, PEG, as such or derivatized with alkyl functions and/or phospholipid, specific ligands for cellular receptors, such as for example vitamins or peptides with ligand function.

In a preferred embodiment, the hydrophilic polymer is a polyethyleneglycol (PEG), preferably having a molecular weight between 500-10,000 daltons and more preferably between 2,000-5,000 daltons. The polyethyleneglycol can be covalently linked to a phospholipidic moiety. Examples of pegylated phospholipids are DPPE-PEG or DSPE-PEG, DMPE-PEG, DAPE-PEG or DOPE-PEG. Particularly preferred phospholipids are DAPC, DSPC, DPPC, DMPA, DPPA, DSPA, DMPG, DPPG, DSPG, DMPS, DPPS, DSPS and Ethyl-DSPC. Most preferred are DPPG, DPPS and DSPC. Mixtures of phospholipids can also be used, such as, for instance, mixtures of DPPE and/or DSPE (including pegylated derivates), DPPC, DSPC and/or DAPC with DSPS, DPPS, DSPA, DPPA, DSPG, DPPG, Ethyl-DSPC and/or Ethyl-DPPC.

Preferably the 1,2-distearoyl-sn-glycero-3-phosphoethanolamine-N-[methoxy(polyethyleneglycol)-2000] (ammonium salt) (DSPE-PEG 2000) is included in the formulation. Preferably this component constitutes up to 16% and even more preferably constitutes about 6-12% of SLNs.

All the materials forming the solid lipid nanoparticle of the present invention are well-known to the person of ordinary skill in the art and normally available on the market.

In one embodiment of the present invention, the composition further includes a targeting moiety having high binding affinity towards diseased tissues. Generally, the targeting moiety must be effective in binding specifically to a target for a disease, so useful to provide an indication of a disease associated to said target. Examples of targets are a cell surface receptor in the form of proteins, enzymes or specific molecules up-regulated in diseases or pathologic tissues. The surface active targeting agent can be composed by a targeting moiety, a lipidic structure and a polymeric spacer between the active moiety and the lipidic structure. In the scopes of the present invention, "targeting moiety" is a molecule, compound, substance capable of establishing a relationship with the target, in any suitable form, for example chemical bond, physico-chemical affinity, chemical reaction, metabolic event. This relationship between said targeting moiety and the target allows the nanoparticle of the present invention to reside in the vicinity of the target for a time sufficient to be detected by the current diagnostic instruments.

A preferred targeting moiety according to the present invention is 1,2-distearoyl-sn-glycero-3-phosphoethanolamine-N-[folate(polyethylene glycol)-2000]ammonium salt (DSPE-PEG2000-Folate). This moiety is herein presented as a representative embodiment for its binding affinity towards the folate receptor. Other representative targeting moieties can also include proteins, aptamers, peptides such as Arg-Gly-Asp (RGD) for αvβ3 integrin targeting and polypeptides, vitamins, antibodies such as bevacizumab, trastuzumab and cetuximab or fragments thereof and carbohydrates that can be incorporated in the nanoparticles of the present invention, preferably after their derivatization with a lipophilic or amphiphilic component, such as alkyl chains or phospholipids for their inclusion in the shell structure around the core of the present SLNs.

Targeting the nanoparticle of the present invention makes it useful as diagnostic agent for those diseases which can be diagnosed also by detecting one or more specific markers. Tumors are a representative example of interest to the present invention.

The component d) is a fluorescent dye of the cyanine family and/or a polyetherocyclic compound including coumarin, pyrano, quinoline, pyranoquinoline, indole and pyranoindole derivates in acid form or a pharmaceutically acceptable salt thereof.

Examples of such fluorescent dye include ICG, cy5, cy5.5, cy7, IRDye®800, IRDye®750 (LI-COR Biosciences), Alexa Fluor® 546, Alexa Fluor® 568, Alexa Fluor® 594, Alexa Fluor® 610, Alexa Fluor® 647, Alexa Fluor® 700 and Fluor® 750 (Invitrogen), DY-682, DY-675, DY-782 (Dyomics GmbH) commercially known as Alexa Fluor® in acid form or a pharmaceutically acceptable salt thereof.

According to the present invention, the fluorescent dye of the cyanine family or a polyetherocyclic compound is selected from the group consisting of:
Indocyanine Green (ICG)

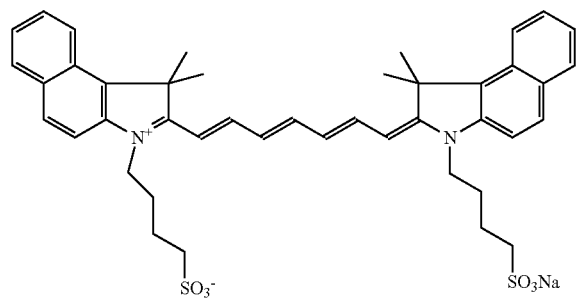

ICG the following compounds, whose chemical structure and the commercial or common name or common code is reported below:
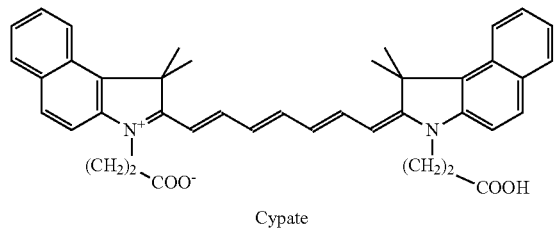
Cypate
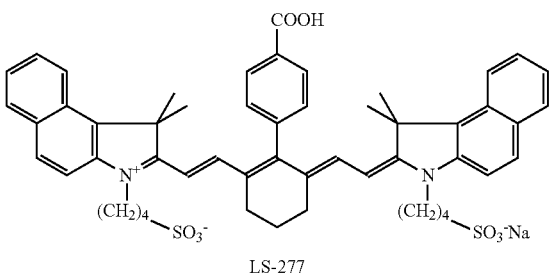
LS-277
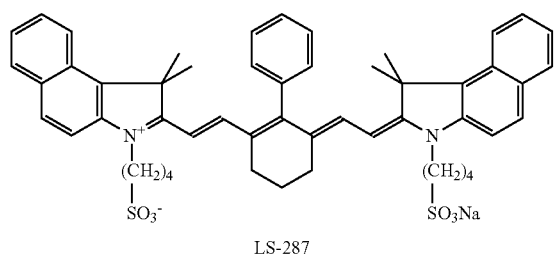
LS-287
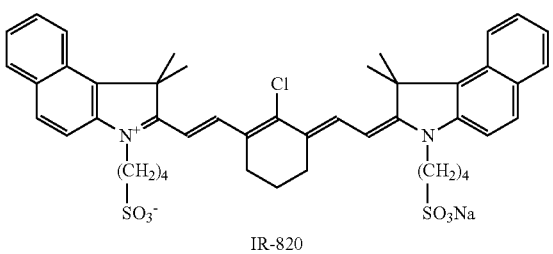
IR-820
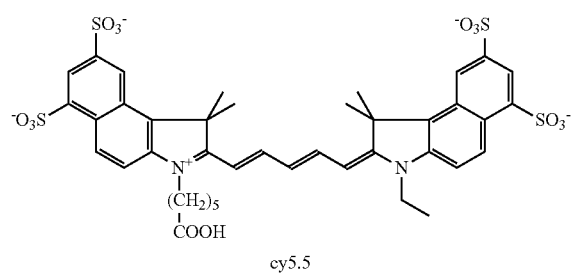
cy5.5
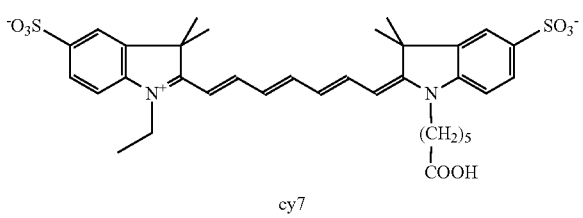
cy7
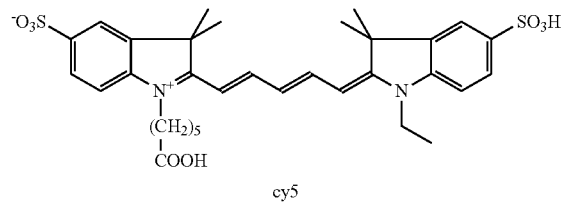
cy5
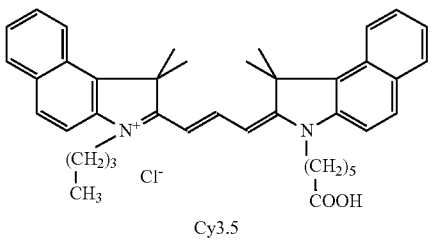
Cy3.5
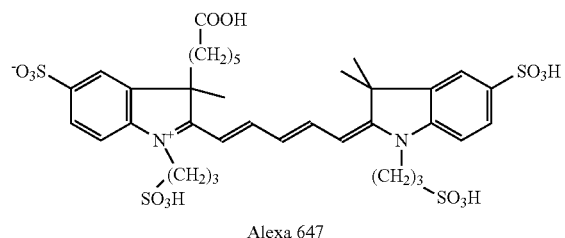
Alexa 647
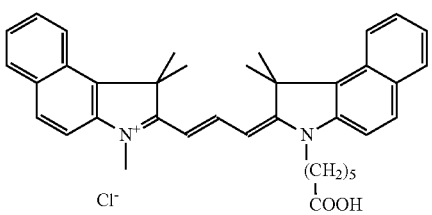
Cy3
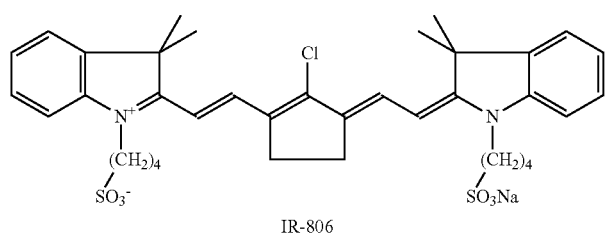
IR-806

-continued
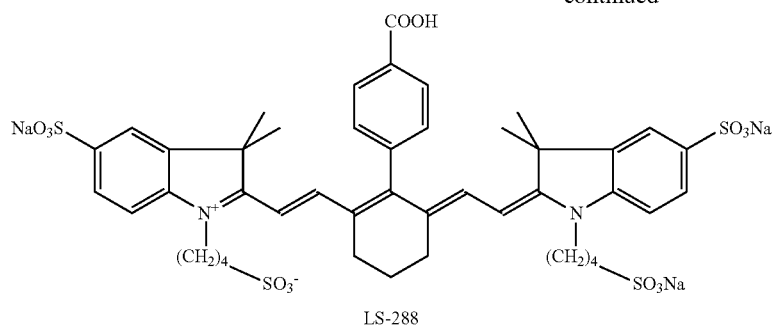
LS-288
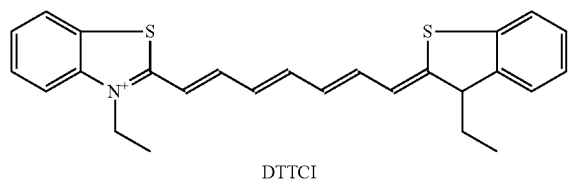
DTTCI
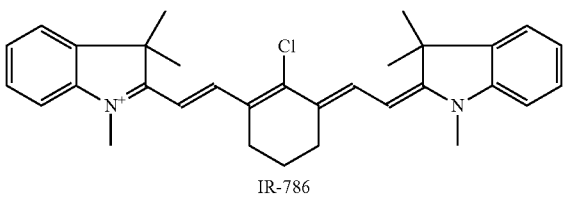
IR-786
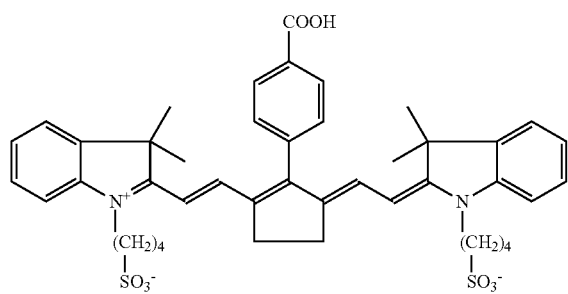
LS-276
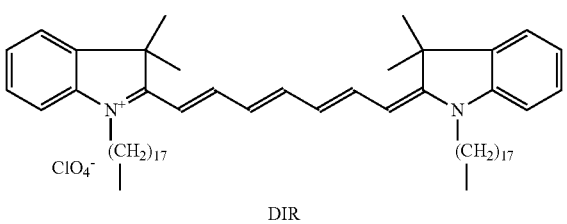
DIR
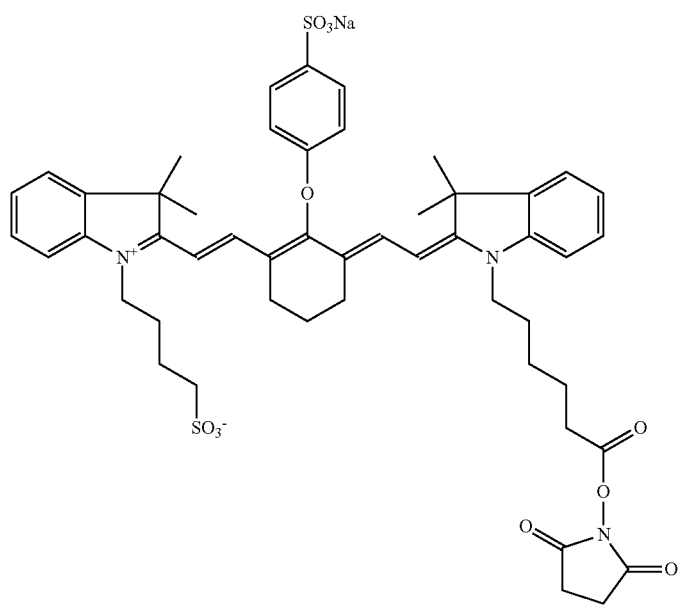
IRDye® 800RS NHS Ester -continued
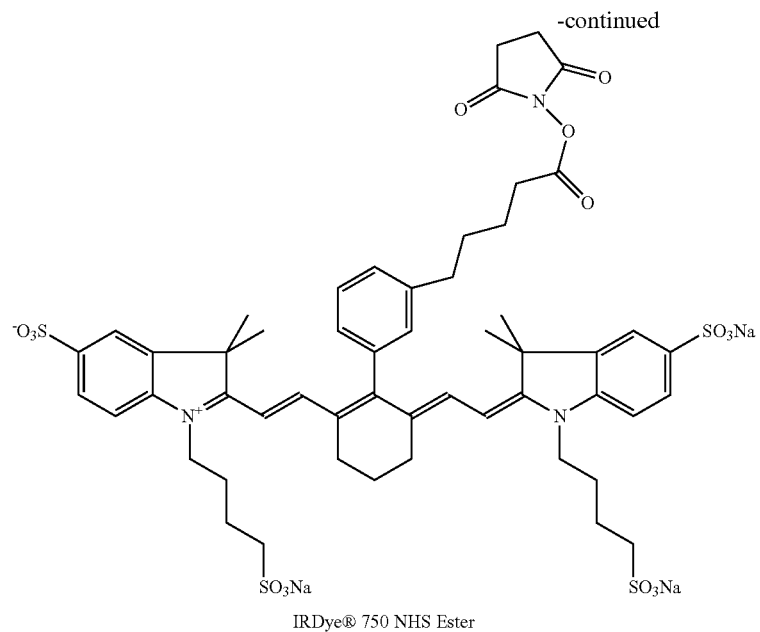
IRDye® 750 NHS Ester
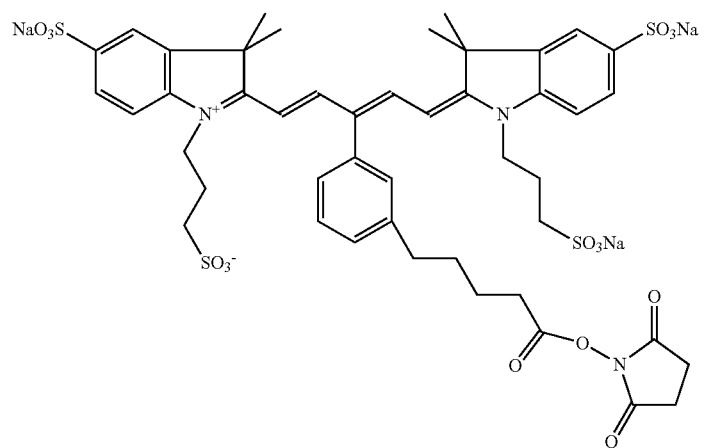
IRDye® 650 NHS Ester
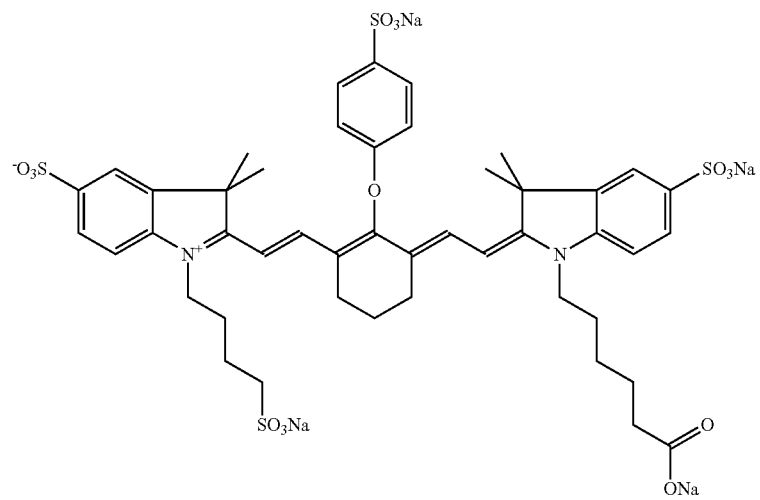
IRDye® 800CW Carboxylate -continued
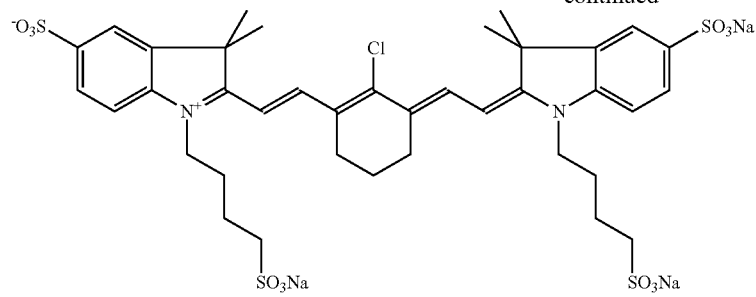
S0456 (Few Chemicals)
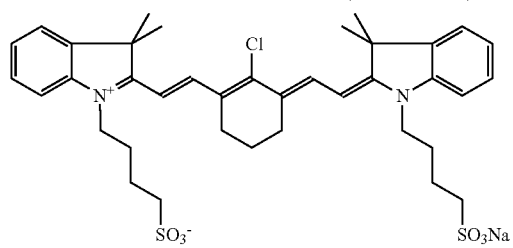
S0121 (Few Chemicals)
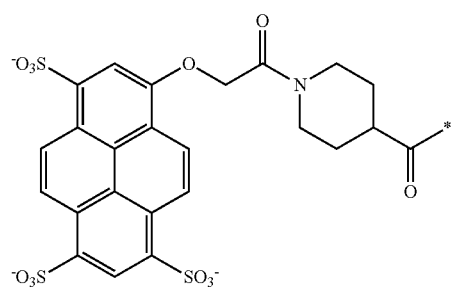
Alexa Fluor® 405
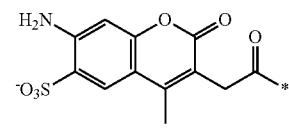
Alexa Fluor® 350
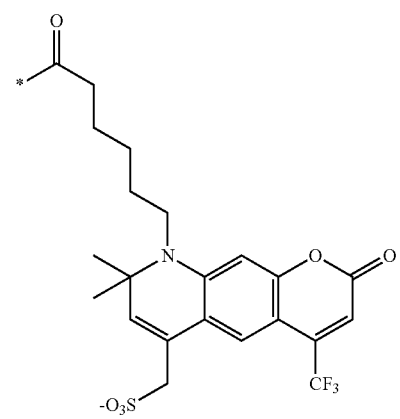
Alexa Fluor® 430
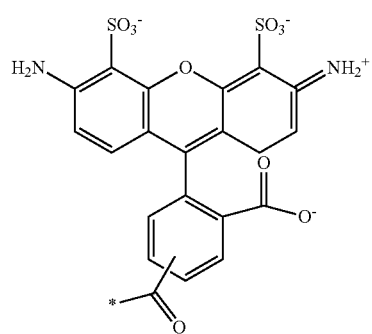
Alexa Fluor® 488
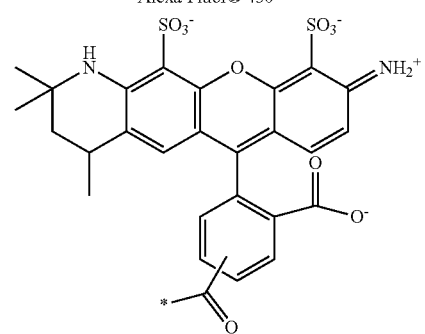
Alexa Fluor® 514
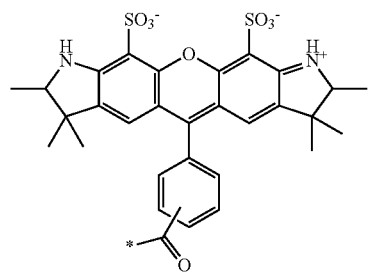
Alexa Fluor® 532
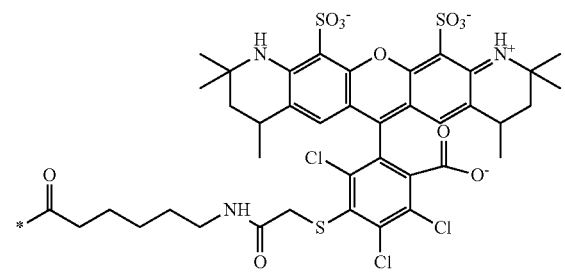
Alexa Fluor® 546

-continued
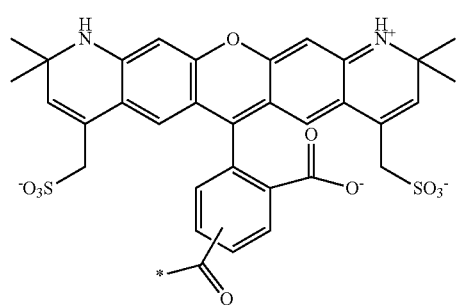
Alexa Fluor® 568
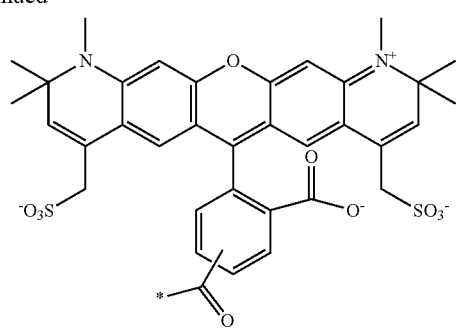
Alexa Fluor® 594
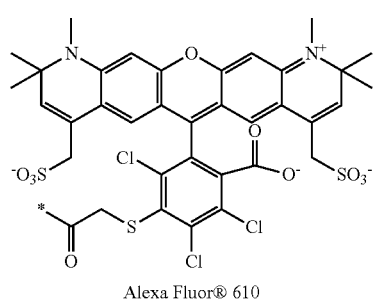
Alexa Fluor® 610
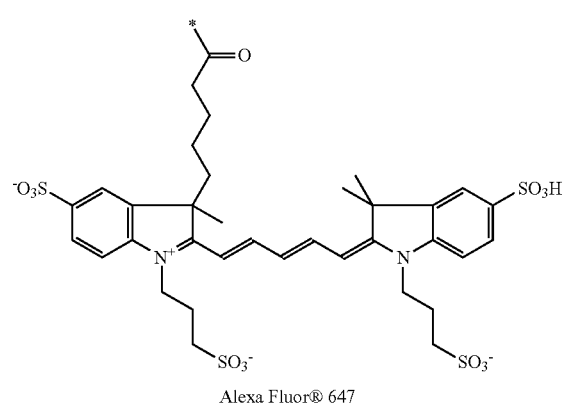
Alexa Fluor® 647
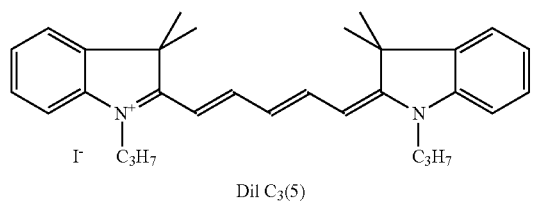
DiI C$_3$(5)
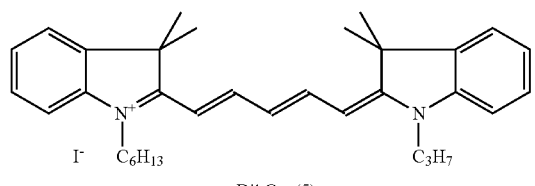
DiI C$_{6,3}$(5)
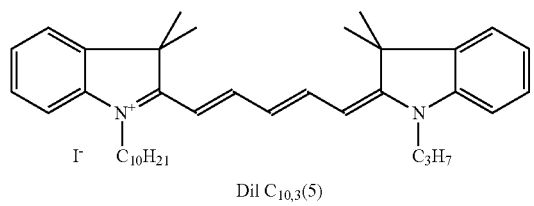
DiI C$_{10,3}$(5)
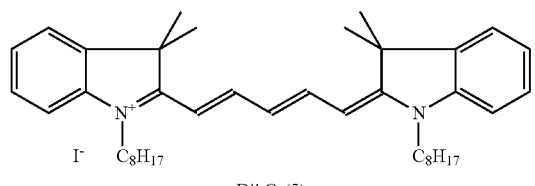
DiI C$_8$(5)
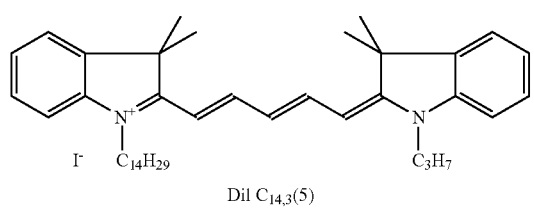
DiI C$_{14,3}$(5)
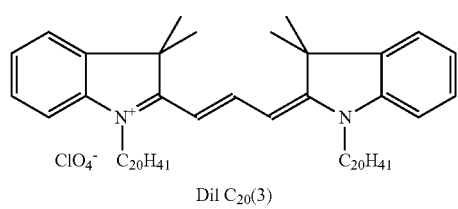
DiI C$_{20}$(3)
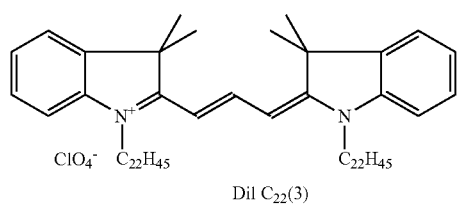
DiI C$_{22}$(3)
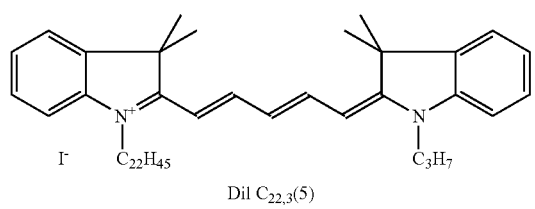
DiI C$_{22,3}$(5)

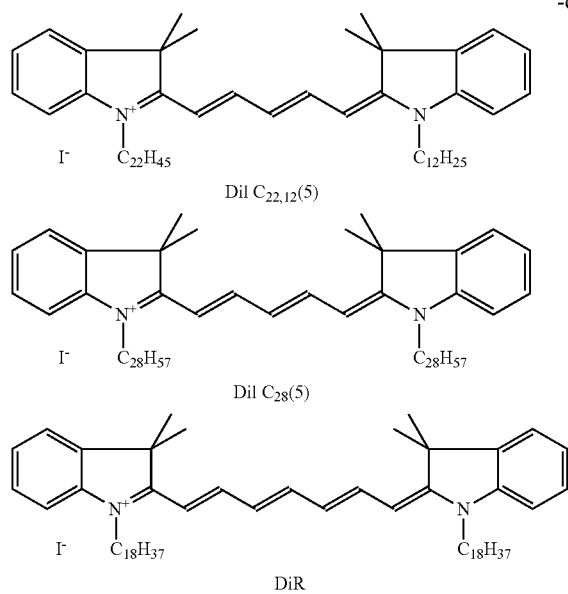

DiI C22,12(5)

DiI C28(5)

DiR

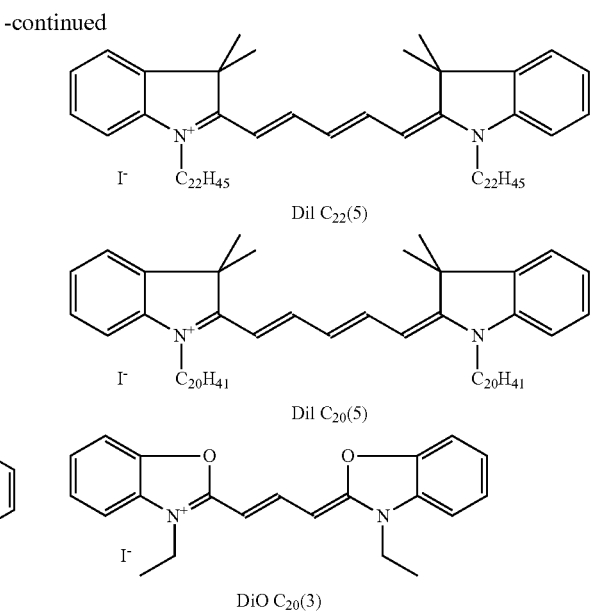

DiI C22(5)

DiI C20(5)

DiO C20(3)

According to a preferred embodiment of the present invention, the fluorescent dye is Indocyanine Green, in any salt form and preferably as sodium salt. The fluorescent dye according to the present invention is present in an amount of 0.01-0.5%, preferably 0.05-0.15%. Generally, the respective ratios among the different components making the solid lipid nanoparticle according to the present invention, can be easily determined by the person of ordinary skill in the art, by resorting to the common general knowledge in this field. See also for example US 2006/0083781 and the references cited therein.

As a guidance to some exemplary embodiments of the present invention, and referring to the theoretical component % weight/weight of the dry SLNs composition, the lipid component forming the core a) is a glyceride and/or a fatty acid comprised in a 30-50%, preferably 35-45% range. The surfactant component b) is preferably made of phospholipids is comprised in the range 25-60%, more preferably 27-45%, even more preferably in the 30-38% range. When used, PEG (component e) is preferably up to about 16%, more preferably 6-12%. %. The stabilizing amphiphilic component c) represents about 4-13%, preferably 8-10%.

The fluorescent dye d) according to the present invention is present in an amount of 0.01-0.5%, preferably 0.05-0.15%.

The present invention also relates to a process for the preparation of the nanoparticles described above.

This process is a modified water/oil/water (W/O/W) method and comprises the following phases:
  i) preparing an organic phase (O) by dissolving in a water immiscible or low-miscible organic solvent a lipid substance or substances, which will form the solid lipid crystalline core a), the amphiphilic compounds which will form the shell b) around said core a), said alkaline-earth complex with a compound of formula I and/or II as defined above comprising the preferred embodiments (component c)), said fluorescent dye of the cyanine family and/or a polyetherocyclic compound d), optionally said hydrophilic polymer e), optionally said targeting moiety f);
  ii) preparing a first aqueous solution (W) by dissolving one or more hydrophilic surfactants and optionally co-surfactants components;
  iii) mixing said organic phase (O) of step i) with said first aqueous solution (W) of step ii) and mixing until a stable W/O micro-emulsion is formed;
  iv) said W/O micro-emulsion obtained in step iii) is subsequently added to a second aqueous solution ($W_1$) which can contain at least a surfactant, to provide a $W/O/W_1$ multiple emulsion;
  v) stripping said organic solvent from the multiple emulsion by evaporation to provide a suspension of lipid nanoparticles;
  vi) cooling down the suspension obtained in step v) to provide the complete crystallization of said solid core a);
  vii) washing said suspension obtained in step vi) from the excess of the components. The so-obtained suspension of SLNs is considered free of hydrophilic surfactant components such as the ionic surfactant and co-surfactant used.
  viii) optionally storing said suspension obtained in step vii) in aqueous phase or in solid phase after water removal.

In step i) the organic solvent is a water-immiscible solvent or a low-water-miscible organic solvent. This kind of organic solvent is well-known in the art and is part of the general knowledge in the chemistry field. For the purposes of the present invention, said organic solvent can have low boiling point, from 20° C. to 70° C. This low-boiling point can be determined at atmospheric pressure or under controlled vacuum condition, as usual practice in this field. In a preferred embodiment, said organic solvent is selected from the group consisting of methylene chloride, 1,2-dichloroethane, chloroform, diethyl ether, ethylacetate, methylacetate and ethyl formate or a mixture thereof. In a more preferred embodiment methylene chloride is used. The solution is preferentially heated to 30-35° C.

In a preferred embodiment of step ii), taurocholic acid sodium salt hydrate and 1-butanol are dissolved in the aqueous phase. Other hydrophilic components can be introduced into the SLN by dissolution in the aqueous or in the organic phase, for example hydrophilic polymeric functions having the function of stealth agents (see component d. above) and/or active targeting agents (see component e. above). In case a targeting agent is used, this will be linked to the stealth agent.

In the step iii) said W/O micro-emulsion is obtained dissolving the following components in a solvent mixture ($CH_2Cl_2$:$H_2O$; 1:0.125, v/v) in the following concentration ranges (M):

| Components | $M_{min}$ | $M_{max}$ |
|---|---|---|
| Glycerides | 0.10 | 0.15 |
| Fatty acids | 0.01 | 0.09 |
| Phospholipids | 0.10 | 0.17 |
| Stabilizing agents | 0.01 | 0.04 |
| ICG | 3.4*E−05 | 1.7*E−03 |
| Stealth agent | 0.00 | 0.02 |
| Surfactants | 0.10 | 0.20 |
| Alcohol | 0.60 | 1.20 |

In the step iv) the microemulsion is added to the aqueous solution $W_1$ (at a ratio 1:10 W/O:W, v/v) containing surfactant in the range of 0.12-0.5% w/v preferably 0.24%. In a preferred embodiment, $W_1$ solution contains polyoxyethylene sorbitan monooleate.

In step v) the solvent is preferably evaporated at atmospheric pressure or under controlled vacuum, conveniently, stirring is used for evaporation. The evaporation can also be obtained by increasing the temperature of the multiple emulsion at atmosphere pressure or under controlled vacuum condition. Preferably, the evaporation temperature should not overcome the melting point of the lipid core component.

Step vi) is carried out at a convenient temperature which can be determined by the person of ordinary skill in the art also in function of the composition of the final solid crystalline lipid core. In a preferred embodiment, cooling is made at a temperature in a 4-15° C. range. Preferably the suspension is cooled at a rate comprised from 0.1 and 0.4° C./min, preferably 0.2-0.4 C.°/min, even more preferably 0.3 C.°/min.

The washing procedure of step vii) comprises for example dialyzation, filtration, ultrafiltration or ultracentrifugation procedures. In a preferred embodiment the formulation is ultrafiltrated or lyophilized to provide the "dry" SLNs composition.

Figure 1:
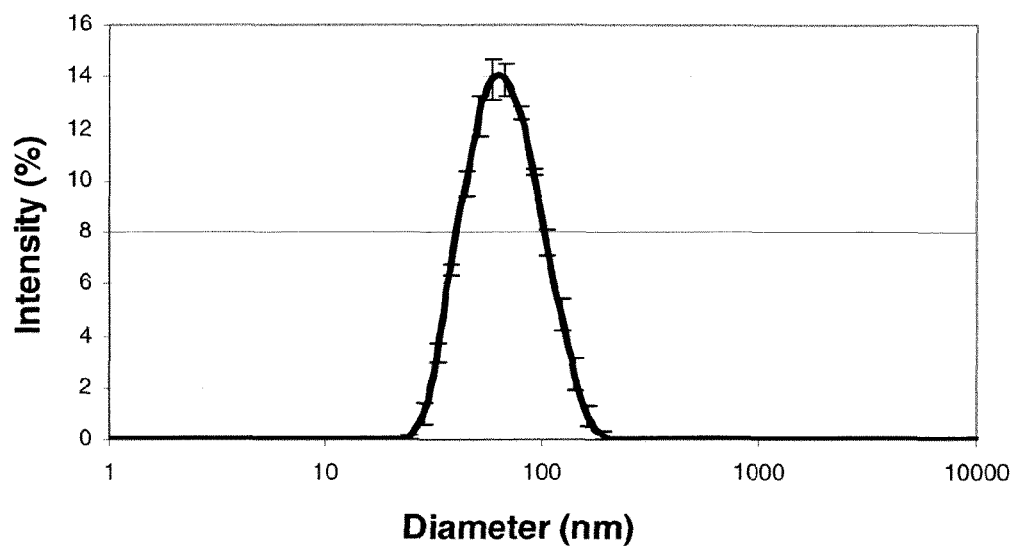
FIG. 1 represents a typical particle size distribution of the ICG-loaded SLNs of the present invention.

In the foregoing description, the present invention is described by means of one preferred embodiment, namely the nanoparticle loaded with Indocyanin Green. However, it is well understood that this description applies to the whole breadth of the invention, namely to all the dyes of the cyanine family and Alexa Fluor® as described in the example from 1 to 6. In one embodiment of the present invention, the fluorescent dye-loaded SLN formulation results in a stable monodisperse colloidal suspension (see FIG. 1, in the embodiment loaded with ICG) preferably having a particle size distribution from 10 to 220 nm, a mean particle size (z-average) lower than 100 nm and a polydispersion index lower than 0.2. In an embodiment of the present invention, ICG-loaded SLNs have a z-average of about 60 nm and a polydispersion index (PdI) of 0.16 (see Table A, showing the SLN of Example 1, 60R012001L; Example 2, 63R011013L; Example 3, 60R012002L; Example 4, 63R011005L; Example 5, 63R011001L; Example 6, 63R011002L).

TABLE A

Targeted and untargeted ICG loaded SLNs physico-chemical characterization.

| | z-average (nm) | SD | PDI | SD | ZP (mV) | SD |
|---|---|---|---|---|---|---|
| Targeted ICG loaded SLNs | | | | | | |
| 63R011005L | 63.0 | 0.7 | 0.14 | 0.02 | −13.87 | 0.85 |
| 63R011001L | 58.4 | 0.5 | 0.18 | 0.01 | −13.33 | 0.38 |
| 63R011002L | 64.3 | 1.2 | 0.15 | 0.10 | −14.76 | 0.97 |
| Untargeted ICG loaded SLNs | | | | | | |
| 60R011013L | 71.7 | 1.0 | 0.15 | 0.01 | −13.08 | 0.43 |
| 60R012001L | 55.0 | 0.4 | 0.18 | 0.01 | −13.41 | 1.05 |
| 60R012002L | 66.1 | 0.3 | 0.17 | 0.01 | −15.59 | 0.27 |

The repeatability of the process of the present invention has been evaluated either for targeted and untargeted ICG-loaded SLNs formulation by the analysis of the averaged physico-chemical parameters, their standard deviation and their relative standard deviation for three different prepared batches.

TABLE B

Repeatability (on 3 batches shown in Table A) of the ICG loaded SLNs formulation method for targeted and untargeted nanoparticles.

| | average | SD | RSD % |
|---|---|---|---|
| z-average (nm) | | | |
| Targeted ICG loaded SLNs | 61.9 | 3.10 | 5.01 |
| Untargeted ICG loaded SLNs | 64.3 | 8.50 | 13.23 |
| PDI | | | |
| Targeted ICG loaded SLNs | 0.16 | 0.021 | 13.29 |
| Untargeted ICG loaded SLNs | 0.17 | 0.015 | 9.17 |
| ZP (mV) | | | |
| Targeted ICG loaded SLNs | −13.99 | 0.722 | 5.16 |
| Untargeted ICG loaded SLNs | −14.03 | 1.364 | 9.72 |

Results listed in Table B (Examples 1-6) show a good repeatability of the process preparation. Furthermore, it is noteworthy that there are no relevant differences on the final physico-chemical parameters of ICG loaded SLNs depending on the incorporation of the targeting moiety.

The nanoparticles according to the present invention are capable of significantly improving the fluorescence emission efficiency of the dye therein incorporated if compared to the free dye. For example, in the representative embodiment with ICG-loaded SLN, ICG fluorescence emission quantum yields % 0%) in water solution is about 2.72%, whereas the corresponding SLN according to the present invention shows a fluorescence efficiency of about 7.6% (see Table C, Example 2 and 4) either for targeted and untargeted SLNs which remains stable over the time at store condition (at least >60 days).

TABLE C

Φ % of ICG dye in water and after incorporation in the SLNs.

| Medium | ICG Φ % | SD |
|---|---|---|
| $H_2O$ | 2.72 | 0.26 |
| Targeted ICG loaded SLNs, 63R011005L | 7.6 | 0.31 |
| Untargeted ICG loaded SLNs, 60R011013L | 7.6 | 0.25 |

TABLE C-continued

Φ % of ICG dye in water and after incorporation in the SLNs.

| Medium | ICG Φ % | SD |
|---|---|---|
| Untargeted ICG loaded SLNs, 60R011013L after 2 months from formulation | 7.5 | 1.14 |

A further advantage of the present invention is the improved photostability of the dye with respect to the free dye in water solution. An experiment was performed in aqueous medium by the exposition of free ICG solution and the ICG loaded SLNs suspension to a 785 nm laser radiation (see FIG. 2, Example 8). The fluorescence emissions were collected by NIR fluorescent imaging system (Pearl® Impulse system by LI-COR Biosciences). The concentrations of the samples were adjusted to display initial comparable fluorescence emission signal. Then, the experiment was carried out in duplicate at 37° C. irradiating both samples for 3 sec and keeping the samples in the dark for 1 sec. This sequence was repeated in continuous for 1 h. From FIG. 2, it is noteworthy that ICG loaded on SLNs shows a higher photostability than the free dye, which is characterized by a faster decreasing in the fluorescent signal during the time. At the end of the experiment, ICG loaded SLNs still show the 50% of the initial emission fluorescence efficiency, whereas fluorescence emission of free ICG is slightly above zero.

Figure 3:
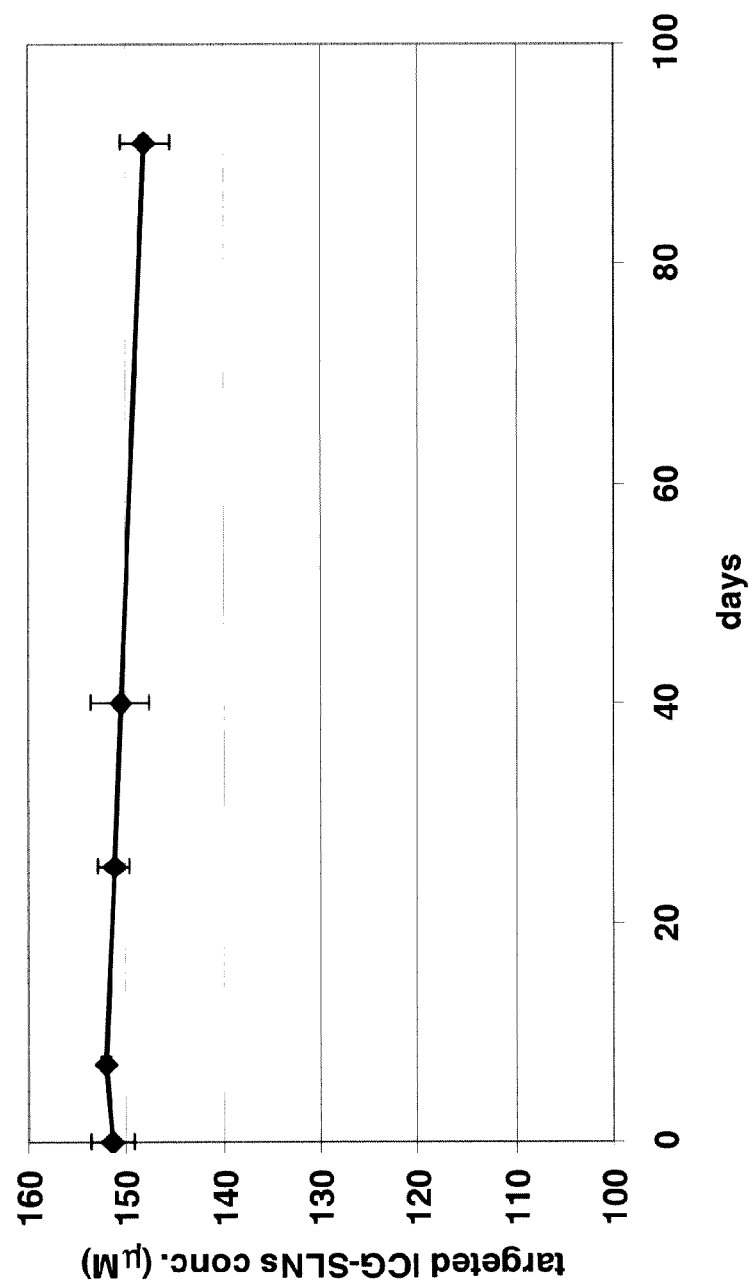
FIG. 3 represents ICG-loaded SLNs long term stability.

As another advantage of the present invention, the long term stability of the dye-loaded SLN is improved. Stability was analyzed by keeping the samples in the dark at storage condition (4° C.) and by measuring the absorption maximum by the UV-Vis spectrophotometer (Lambda 40, Perkin Elmer). ICG loaded SLN were dissolved in an organic solvent mixture ($CHCl_3$:$CH_3OH$ 2:1) and further diluted for UV-Vis analysis at 800 nm. Calibration curve was used for the calculation of ICG concentration formulated in the SLNs. Data in FIG. 3 (Example 9) show that the ICG loaded SLNs concentration, measured at different time point during 90 days from the formulation date, can be recovered at 95% with respect to the initial value.

Another advantage of the present invention is the remarkably decreased rate of aggregates formation respect to the free ICG in aqueous solution. In FIG. 4 (panel A, Example 7) there are reported the UV-Vis spectra of ICG-loaded SLNs suspension just after the formulation date and 90 and 120 days later. It is evident that the presence of aggregates (so called J-aggregates) after 120 days is not significant and the absorbance spectrum of ICG loaded SLNs in the observed spectral range still remains essentially the same. The absorbance at 800 nm is recovered at 96% with respect to the initial value. In addition, the fluorescence emission properties can be preserved by the incorporation of ICG in the SLNs over the observed period of time (data not shown). On the other hand, it is known that ICG at μM concentration can aggregate in few days (see FIG. 4 B, Example 7) with consequent decreasing of the absorbance (at 780 nm) of the free ICG and growing of a new peak at 900 nm during the storage time.

Another advantage provided by the present invention is the enhanced stability of particle size distribution, surface charge and PdI, which were measured at different time points keeping the formulation in the dark, at 4° C. and carrying out the measurements at 25° C. Results listed in Table D, Example 4 show that after 90 days from the formulation, the physico-chemical parameters do not evidence any significant variation.

TABLE D

Physico-chemical stability of targeted ICG loaded SLNs (shown in Example 4)

| Days | Z-average (nm) | SD | PdI | SD | Z-pot (mV) | SD |
|---|---|---|---|---|---|---|
| 6 | 63.00 | 0.75 | 0.140 | 0.020 | −13.87 | 0.85 |
| 90 | 68.50 | 0.92 | 0.152 | 0.004 | −14.26 | 0.27 |

In a further aspect, the present invention deals with the specific uptake of the targeted ICG loaded SLNs towards a specific receptor. In an exemplary embodiments, FA-ICG-loaded SLN was evaluated in terms of binding properties on the folate receptor. The experiment was carried out by biolayer interferometry system (Octet® instrument, Fortebio). Two different batches of targeted and untargeted ICG-loaded SLN were analyzed for their binding properties toward a biosensor coated with anti folic acid IgG (FA2) conjugated via protein A. In FIG. 5, Example 10, results show that targeted ICG loaded SLNs bound IgG anti folate with good affinity, respect to the untargeted ones, which do not recognize pre-activated biosensor.

The present invention also relates to the improved tissue targeting properties of ICG loaded SLN herein disclosed in vivo applications. In one embodiment, the specific uptake towards the tumor tissues of the F-ICG loaded SLNs was evaluated specifically on an ovarian carcinoma xenograft model using IGROV-1 cell line subcutaneously injected in the right flank of Balb/C nu/nu mice. The acquired fluorescence signal was collected in a region of interest drawn around the tumor area and referred to the background fluorescence of the muscle. In the case of FA-ICG loaded SLNs, the measured in vivo fluorescence signal was 5.1 a.u. (SD 2.9), whereas in the case of untargeted ICG loaded SLNs administration, the fluorescence signal was 1.7 (SD 0.2).

Animals were subsequently sacrificed in order to quantify the fluorescence signals in each excised organs from ex-vivo imaging analysis. In FIG. 6, Example 11 all measured fluorescence signals of the analyzed tissues are reported. It is noteworthy that the specific uptake of the FA-ICG loaded SLNs on the tumor tissues is confirmed. In particular, the ex vivo fluorescence ratio of the targeted ICG loaded SLNs in comparison to untargeted was enhanced by a factor of 3 (measured as (tumor SI-muscle SI)/muscle SI). Furthermore, both formulations seem to follow the same clearance mechanisms involving mainly liver and kidney metabolic pathways. In FIG. 7, Example 11 are also reported the ex vivo imaging analysis from two representative mice sacrificed at 24 h after administration of targeted and untargeted ICG loaded SLNs.

The SLNs according to the present invention offer several advantages with respect to other carrier systems. For example, fat emulsions or nanoemulsions have been proposed as delivery system for lipophilic drugs, which can easily be incorporated into the oil droplets. These carrier systems allow the reduction of side effects but they are thermodynamically unstable. Therefore, emulsions often tend to agglomerate or even break and the drug is rapidly released once they reach the blood stream.

With respect to liposomes, SLN can be formulated at very small diameters, lower than 60 nm which are not compatible with stable liposomes, where the excess of surface curvature cause the instability of liposomial formulations, inhibiting to a certain extent their practical use.

The size of nanoparticles is a very important parameter that strongly affects their accumulation in the pathological tissues. It has been demonstrated that large differences can occur in the distribution of nanoparticles in cancer tissues simply by varying their size. It was suggested that optimal accumulation can be obtained for particles having a diameter lower than 60 nm which is a more reachable size for stable SLNs than for liposome preparations.

The SLN according to the present invention, in the representative embodiment of ICG-loaded nanoparticles, show very high optical and colloidal stability compared with formulation described in the prior art (40 days in WO2010/018216 and 25 days in WO2003/057259).

Actually, in a representation of the invention the optical density of a targeted ICG-loaded SLNs was measured until 170 days after formulation resulting in very stable observed values (OD at 170 days was >95% respect to the initial value). The measurements were carried out with a Perkin Elmer Lambda 40 UV-Vis spectrophotometer (see FIG. 8).

In a representation of the invention, the measure fluorescence emission efficiency of ICG-loaded SLNs was equal to 7.6% (see Table C) either for targeted or untargeted SLNs. Moreover the fluorescence quantum yields remains stable over the time (at least >60 days) as it is show for ICG loaded SLNs formulated as described in the example 2. Furthermore, ICG-loaded SLNs fluorescence quantum yields is 2.8 time higher than ICG in water. This property is a significant and unexpected improvement with respect to the prior art described in WO2010/018216, which shows a fluorescence quantum yields of a ICG nanoemulsion (400 µM) only 2 times higher than ICG in water solution (see Table 2 and column label F).

Additional optical features (i.e. maximum absorption and emission wavelengths, Stokes' shifts) of ICG in aqueous medium and after incorporation in the SLNs are reported in Table E.

TABLE E

Optical properties of ICG loaded SLNs formulation (example 4).

| Medium | A max wavelength (nm) | Fluor. Emission λmax (nm) | Stokes' shift |
|---|---|---|---|
| ICG loaded SLNs | 800 | 832 | 32 |
| ICG (H$_2$O) | 780 | 809 | 29 |

It is clear that the interaction of ICG with SLNs components, demonstrated by the high red-shift of the absorption and emission maxima with respect to ICG in water solution, highly improves ICG in vivo optical imaging applications.

ICG-SLN according to the present invention shows also improved uploading with respect to prior art. The mean yield of uploaded ICG, calculated as the amount of ICG in the final formulation with respect to the theoretical amount, was higher than 75% up to 90% (no ICG was detectable in the external phase). WO2010/018216 shows value close to 35%. Furthermore, a study of ICG entrapment versus the initial ICG loading concentration was performed by Navarro et al. resulting in an increase (>40%) of the entrapment efficiency with the increasing of the initial concentration. In our formulation process it was possible to obtain high entrapment efficiency even when the initial ICG concentration was lower than 1 mM.

The following examples further illustrate the invention.

EXPERIMENTAL PART

Preparation of Compounds of Formula (I)

Preparation 1: Preparation of Compound 8 According to the Scheme 3

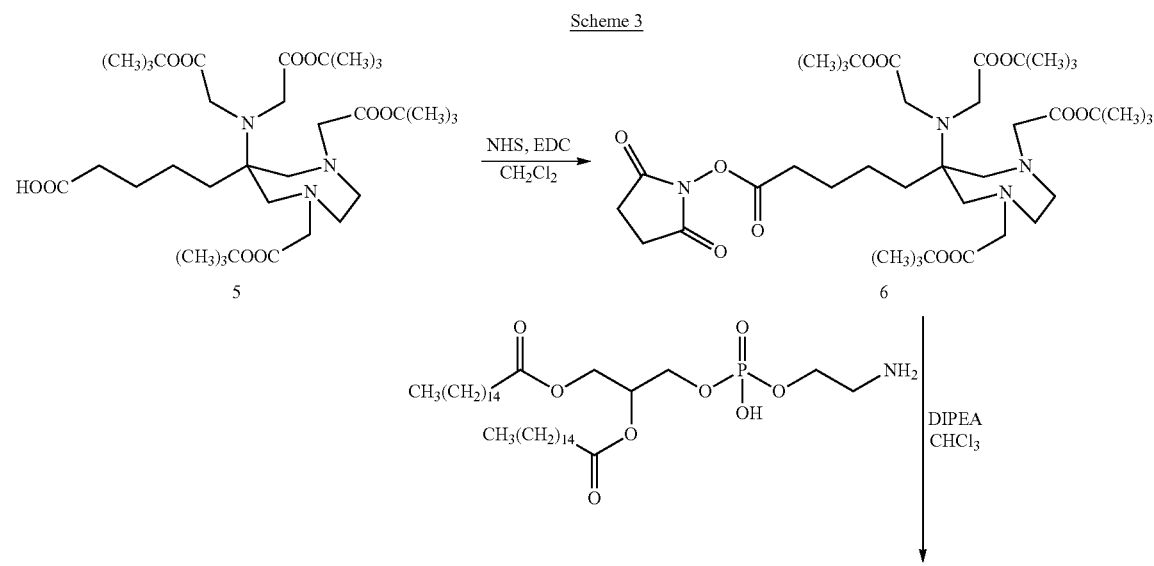

Scheme 3

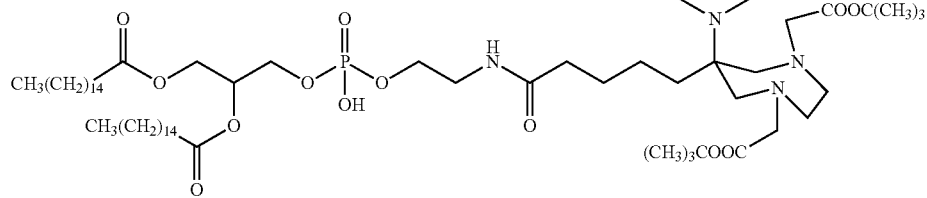

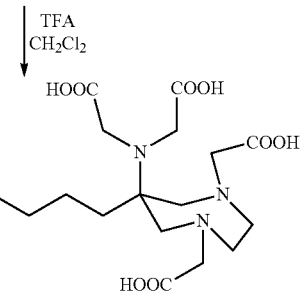

Preparation 1.1: Preparation of Compound 5

Compound 5 was prepared in five steps according to the procedure described in US2006018830 as illustrated in the Scheme 2 below.

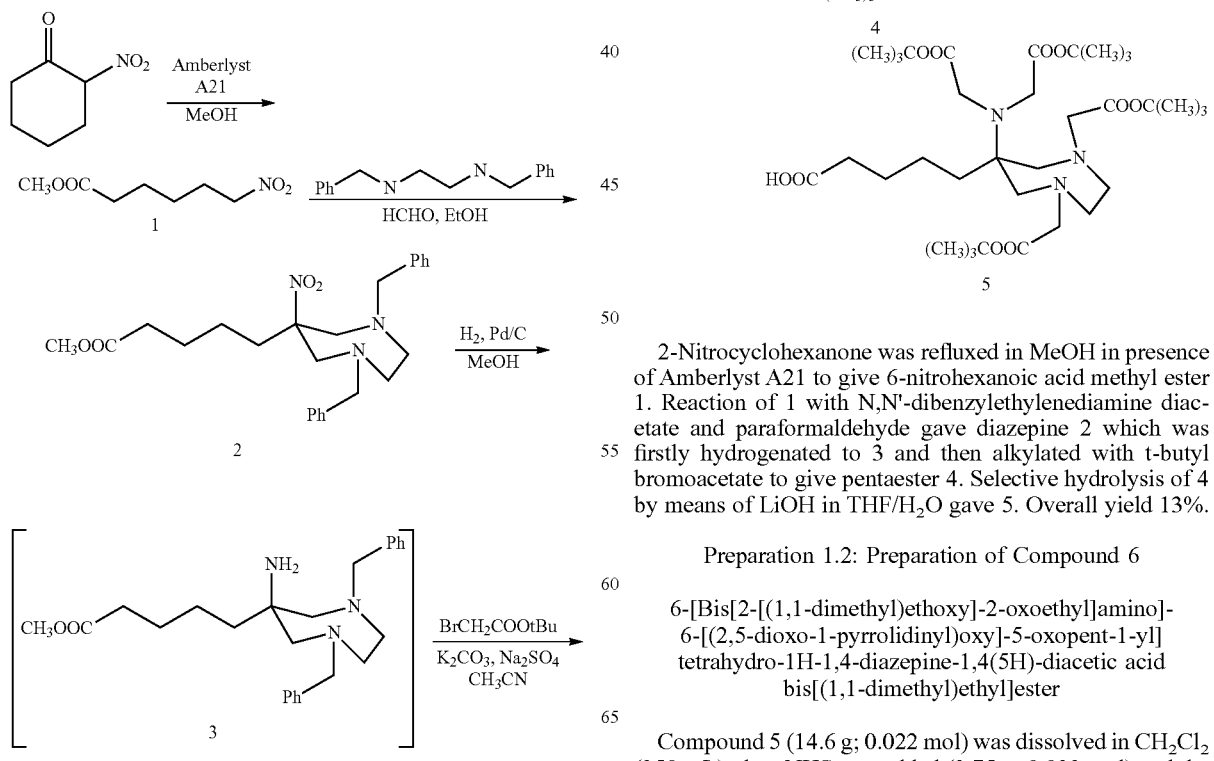

2-Nitrocyclohexanone was refluxed in MeOH in presence of Amberlyst A21 to give 6-nitrohexanoic acid methyl ester 1. Reaction of 1 with N,N'-dibenzylethylenediamine diacetate and paraformaldehyde gave diazepine 2 which was firstly hydrogenated to 3 and then alkylated with t-butyl bromoacetate to give pentaester 4. Selective hydrolysis of 4 by means of LiOH in THF/H₂O gave 5. Overall yield 13%.

Preparation 1.2: Preparation of Compound 6

6-[Bis[2-[(1,1-dimethyl)ethoxy]-2-oxoethyl]amino]-6-[(2,5-dioxo-1-pyrrolidinyl)oxy]-5-oxopent-1-yl] tetrahydro-1H-1,4-diazepine-1,4(5H)-diacetic acid bis[(1,1-dimethyl)ethyl]ester Compound 5 (14.6 g; 0.022 mol) was dissolved in CH₂Cl₂ (350 mL), then NHS was added (3.75 g; 0.033 mol) and the mixture was cooled to 0° C. in an ice-bath. A solution of EDC (6.25 g; 0.033 mol) in $CH_2Cl_2$ (150 mL) was added dropwise, then the reaction solution was stirred for 24 h at room temperature. The mixture was washed with $H_2O$ (3×150 mL). The organic phase was dried ($Na_2SO_4$), filtered and evaporated to give 6 as a yellow oil (15.42 g; 0.020 mol). Yield 92%.

Analytical Data:
Mr: 768.94 (C38H64N4O12)
1H- and 13C-NMR and MS are compatible with the structure Preparation 1.3: Preparation of compound 7 (6-[Bis[2-[(1,1dimethyl)ethoxy]-2-oxoethyl]amino]-6-[(13R)-10-hydroxy-10-oxido-5,16-dioxo-13-(1-oxo-decyl)oxy]-9,11,15-trioxa-6-aza-10-phosphanonacos-1-yl]-tetrahydro-1H-1,4-diazepine-1,4(5H)-diacetic acid bis[(1,1-dimethyl)ethyl]ester)

Compound 6 (1.92 g; 2.50 mmol) was dissolved in $CHCl_3$ (190 mL). Dipalmitoyl-sn-glycero-3-phosphoethanolamine DPPE (1.73 g; 2.50 mmol) and diisopropylethylamine (DIPEA) (1.7 eq) were added in this order. The solution was stirred at room temperature from 3 h to 24 h. The mixture was sequentially washed with $H_2O$ (1×50 mL), acidified $H_2O$ (pH 4-5 with HCl; 1×50 mL) and $H_2O$ (1×50 mL). The organic phase was dried ($Na_2SO_4$), filtered and evaporated. The crude material thus obtained was purified by flash chromatography to give compound 7 (2.79 g; 2.07 mmol) as a white solid material. Yield 83%.

Analytical Data:
HPLC-ELSD: 100% (area %); Mr: 1345.82 (C71H133N4O17P)
$^1$H- and $^{13}$C-NMR and MS are compatible with the structure.

Preparation 1.4: Preparation of Compound 8 (6-[Bis[(carboxymethyl)amino]-6-[(13R)-10-hydroxy-10-oxido-5,16-dioxo-13-(1-oxodecyl)oxy]-9,11,15-trioxa-6-aza-10-phosphanonacos-1-yl]-tetrahydro-1H-1,4-diazepine-1,4(5H)-diacetic acid)

Compound 7 (2.79 g; 2.07 mmol) was dissolved in $CH_2Cl_2$ (100 mL) and the solution was stirred and cooled at 0° C., then TFA (6 eq) was added dropwise. The reaction mixture was stirred for 1 h at room temperature. The solution was evaporated and the residue dissolved in fresh TFA (30 eq). This solution was stirred for 80 h at room temperature; the reaction was monitored by MS analysis and HPLC-ELSD. The mixture was evaporated and the residue was treated with diisopropyl ether to obtain a white solid that was centrifuged and washed with diisopropyl ether (2×30 mL). That solid was suspended in $H_2O$, dissolved at pH 6-7 by addition of 5% aq $NaHCO_3$ and precipitated at pH 2 by addition of 1M HCl. The solid was filtered and dried at reduced pressure ($P_2O_5$) to obtain the ligands 8 (1.77 g; 1.58 mmol) as a white solid material. Yield 76%.

Analytical Data:
HPLC-ELSD: 95.3% (area %)
Mr: 1121.39 (C55H101N4O17P)
Complexometric titer: 95.7%
$^1$H- and $^{13}$C-NMR and MS are compatible with the structure.

Preparation 2: Preparation of Compound 10 According to the Scheme 4

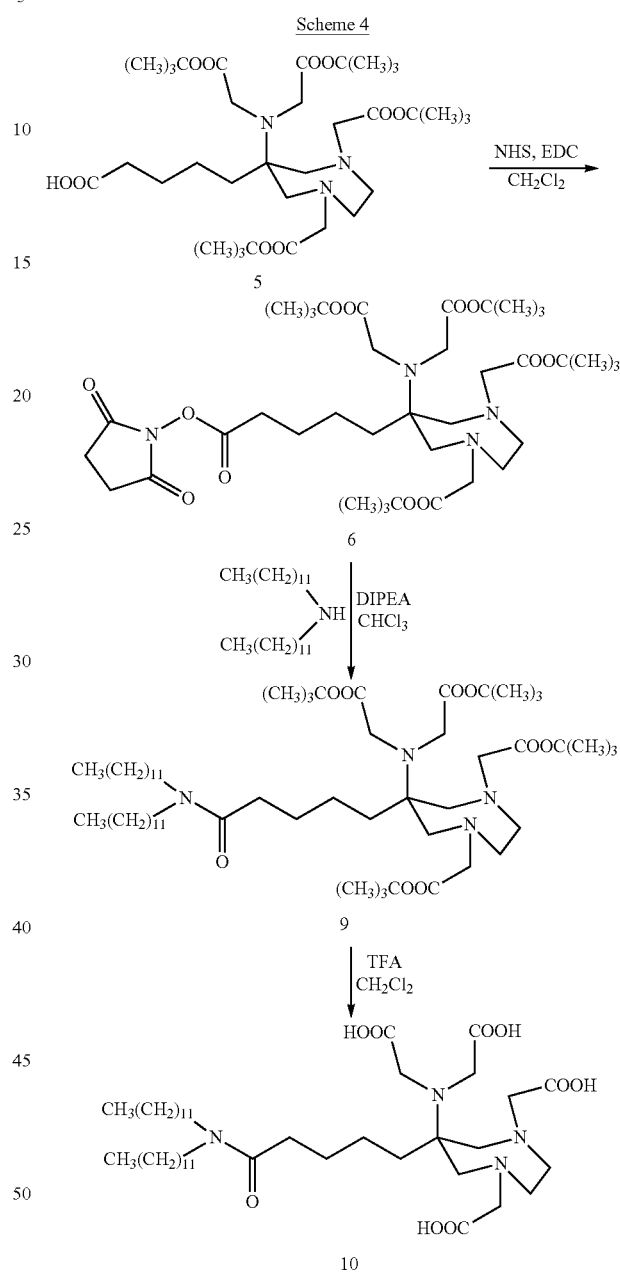

Preparation 2.1: Preparation of Compound 9 (6-[Bis[2-[(1,1-dimethyl)ethoxy]-2-oxoethyl]amino]-6-[5-(dodecylamino)-5-oxopent-1-yl]-tetrahydro-1H-1,4-diazepine-1,4(5H)-diacetic acid-bis[(1,1-dimethyl)ethyl]ester)

Compound 6 prepared according to Preparation 1.2 (3.13 g; 4.07 mmol) was dissolved in $CHCl_3$ (200 mL) with didodecylamine (1.44 g; 4.07 mmol) and DIPEA (1.7 eq). The reaction solution was stirred at room temperature for 24 h and was subsequently washed with $H_2O$ (1×50 mL), acidified $H_2O$ (pH 4-5 with HCl; 1×70 mL) and $H_2O$ (1×50 mL). The organic phase was dried (Na$_2$SO$_4$), filtered and evaporated. The so-obtained product was purified by flash chromatography to give compounds 9 (4.30 g, 4.27 mmol) as an oil. Quantitative yield.

Analytical Data:
HPLC-ELSD: 89.7% (area %);
Mr: 1007.53 (C58H110N4O9).
$^1$H- and $^{13}$C-NMR and MS are compatible with the structure.

Preparation 2.2: Preparation of Compounds 10 (6-[Bis[(carboxymethyl)amino]-6-[5-(dodecylamino)-5-oxopent-1-yl]-tetrahydro-1H-1,4-diazepine-1,4(5H)-diacetic acid]

Compounds 9 (4.30 g, 4.27 mmol) was dissolved in CH$_2$Cl$_2$ (50 mL) and the so-obtained solution was stirred and cooled to 0° C., then TFA (6 eq) was added dropwise. The reaction mixture was stirred for 1 h at room temperature. The solvent was evaporated and the obtained residue was dissolved in fresh TFA (50 eq). This solution was stirred for 80 h. The mixture was evaporated and the residue was treated with diisopropyl ether (70 mL) to obtain a white precipitate that was filtered or centrifuged, washed with diisopropyl ether (2×20 mL) and dried at reduced pressure (P$_2$O$_5$; NaOH pellets) to obtain crude ligand as white solid. The crude product was resuspended in H$_2$O, dissolved at pH 6-7 by addition of 2N NaOH and precipitated at pH 2 by addition of 1M HCl to give the ligand 10 (2.83 g, 3.61 mmol) as white solid. Yield: 85%.

Analytical Data:
HPLC-ELSD: 82.4% (area %).
Mr: 783.10 (C$_{42}$H$_{78}$N$_4$O$_9$).
$^1$H- and $^{13}$C-NMR and MS are compatible with the structure.

1.1 Preparation of the Compounds of Formula (II)

1.2 Preparation 3: Preparation of Compound 13 According to the Scheme 5

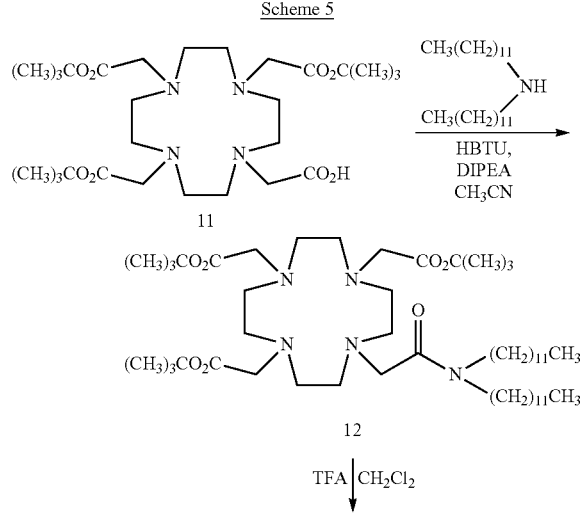

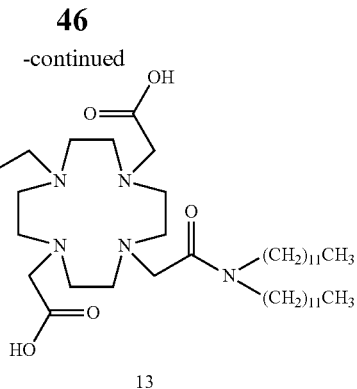

Preparation 3.1: Preparation of Compound 12 (10-[2-(didodecylamino)-2-oxoethyl]-1,4,7,10-tetraazacyclododecane-1,4,7-triacetic acid tris[(1,1-dimethyl)ethyl]ester)

HBTU (1.89 g; 4.95 mmol) and DIPEA (1.09 g; 8.41 mmol) were sequentially added to a suspension of compound 11 (2.84 g; 4.95 mmol) in CH$_3$CN (200. mL) and the mixture was left under stirring at room temperature for 30 min; didodecylamine (1.75. g; 4.95 mmol) was added and the mixture was kept under stirring at room temperature for 24 h.

The reaction mixture was evaporated and the residue was dissolved in CHCl$_3$ and washed sequentially with H$_2$O (100 mL), acidified H$_2$O (pH 4-5 with HCl; 100 mL) and H$_2$O (100 mL). The organic layer was dried (Na$_2$SO$_4$), filtered and evaporated, and the resulting crude material was purified by flash chromatography to obtain compound 12 as a colorless oil (3.55. g; 3.91. mmol). Yield 79.%.

Analytical Data:
Mr: 908.40 (C52H101N5O7)
$^1$H- and $^{13}$C-NMR and MS are compatible with the structure Preparation 3.2: Preparation of Compound 13 and 14 (10-[2-(didodecylamino)-2-oxoethyl]-1,4,7,10-tetraazacyclododecane-1,4,7-triacetic acid, cpd. 13)

TFA (6 eq) was added dropwise to a solution of compound 12 (4.40. g; 4.84. mmol) in CH$_2$Cl$_2$ (70. mL) cooled to 0° C.; the resulting solution was stirred at room temperature for 1 h and then evaporated. The residue was dissolved in fresh TFA (50 eq) and the so-obtained solution was kept under stirring at room temperature for 96 h.

The reaction mixture was evaporated and the residue was treated with iPr$_2$O (150 mL) to give a white solid material which was centrifuged, washed with iPr$_2$O (2×40 mL) and dried to give the ligand 13 as a whitish solid material (2.44. g; 3.30. mmol). Yield 68%.

Analytical Data
Complexometric titer: 99.4.%
Mr: 740.08 (C40H77N5O7)
$^1$H- and $^{13}$C-NMR and MS are compatible with the structure.

Compound 14 was synthesized according to the procedure disclosed in MAGMA 2001.12 (2-3), 114-120.

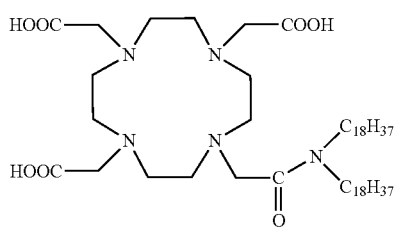

14

Preparation 4: Preparation of Compounds 15a-b

Scheme 6

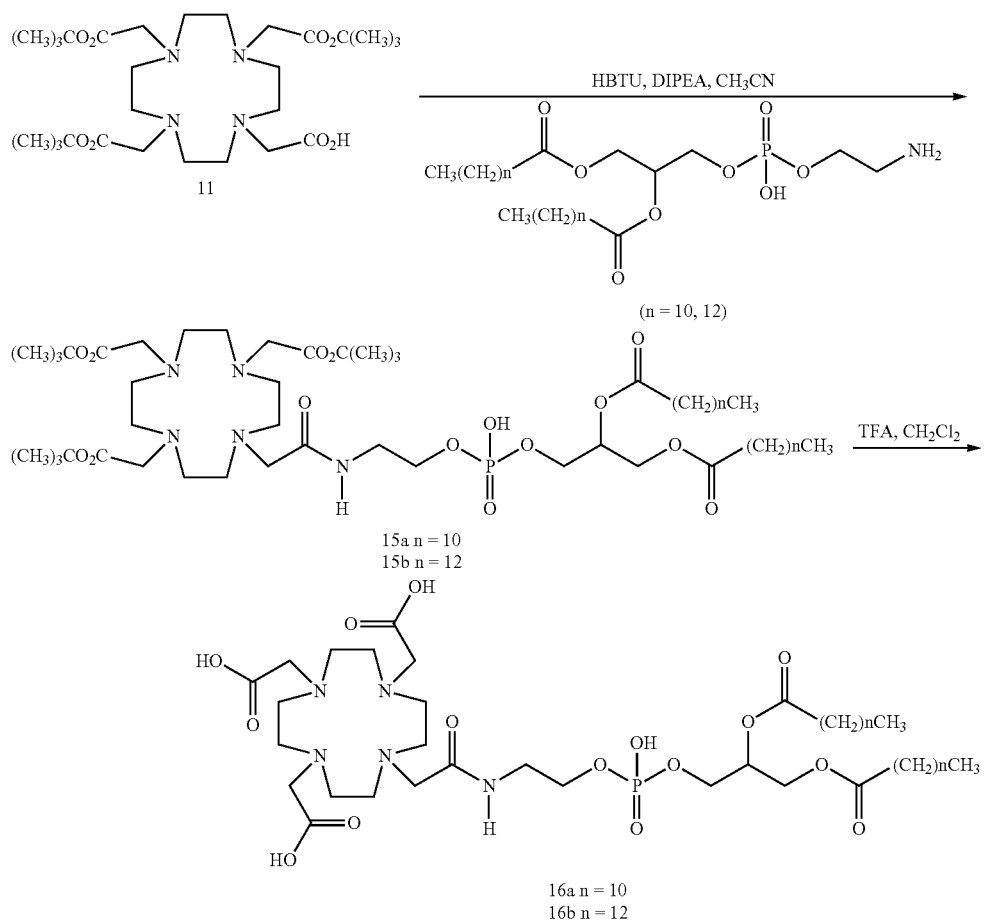

15a n = 10
15b n = 12

16a n = 10
16b n = 12

Preparation 4.1 Preparation of Compounds 15a-b—General Procedure

HBTU (1 eq) and DIPEA (1.7 eq) were sequentially added to a suspension of compound 11 in CH$_2$Cl$_2$ (concentration 1% w/v) and the mixture was kept under stirring at room temperature for 30 min; phosphoethanolamine (DLPE n=10 or DMPE n=12) (1 eq) was then added and the mixture was maintained under stirring at room temperature for 24 h. The reaction mixture was sequentially washed with H$_2$O (100 mL), acidified H$_2$O (pH 4-5 with HCl; 100 mL) and H$_2$O (100 mL). The organic layer was dried (Na$_2$SO$_4$), filtered and evaporated, and the so-obtained crude material was purified by flash chromatography to obtain compounds 15a-b.

Preparation 4.1a Preparation of 10-[(10R)-7-hydroxy-7-oxido-2,13-dioxo-10-[(1-oxododecyl)oxy]-6,8,12-trioxa-3-aza-7-phosphatetracos-1-yl]-1,4,7,10-tetraazacyclododecane-1,4,7-triacetic acid tris[(1,1-dimethyl)ethyl]ester, cpd 15a Reagents: Compound 11 (968 mg; 1.69 mmol); 1,2-didodecanoyl-sn-glycero-3-phosphoethanolamine (980 mg; 1.69 mmol).
Compound 15a (605 mg, 0.53 mmol); Yield 32%.
Analytical Data
HPLC-ELSD: 40.6% (area %)
Mr: 1134.48 (C57H108N5O15P)

$^1$H- and $^{13}$C-NMR and MS are compatible with the structure.

Preparation 4.1b Preparation of 10-[(10R)-7-hydroxy-7-oxido-2,13-dioxo-10-[(1-oxotetradecyl)oxy-6,8,12-trioxa-3-aza-7-phosphaesacos-1-yl]-1,4,7,10-tetraazacyclododecane-1,4,7-triacetic acid tris[(1,1-dimethyl)ethyl]ester, cpd 15b Reagents: Compound 11 (1.43 g; 2.36 mmol), 1,2-ditetradecanoyl-sn-glycero-3-phosphoethanolamine (1.50 g; 2.36 mmol).
Compound 15b (2.18 g, 1.97 mmol). Yield 78%.
Analytical Data
HPLC-ELSD: 82.4% (area %)
Mr: 1190.49 (C61H116N5O15P)

¹H- and ¹³C-NMR and MS are compatible with the structure.

Preparation 4.2: Preparation of Compounds 16a-b—General Procedure

TFA (6 eq) was added dropwise to a solution of compounds 15a-b in CH₂Cl₂ (concentration 1% w/v) cooled to 0° C. and the solution was stirred at room temperature for 1 h and then evaporated. The residue was dissolved in fresh TFA (30 eq) and the new solution was kept under stirring at room temperature for 96 h.

The reaction mixture was evaporated and the residue was treated with iPr₂O (150 mL) to yield a white solid material which was centrifuged and washed with iPr₂O (2×40 mL).

The crude product 16a was purified according to the following method. The crude product was suspended in H₂O and dissolved at pH 6-7 by addition of 5% aq. NaHCO₃ and subsequently re-precipitated at pH 3 by addition of 1M HCl. The so-obtained solid material was centrifuged and dried to obtain ligand 16a.

The crude product 16b was purified according to the following method. The crude product was suspended in H₂O, dissolved at pH 6-7 by addition of 1M NaOH and the so-obtained solution was purified by percolation on Amberlite® XAD1600 resin using a H₂O/CH₃CN gradient as eluent. Fractions containing the desired product were combined and lyophilized to obtain ligand 16b.

Preparation 4.2a Preparation of 10-[(10R)-7-hydroxy-7-oxido-2,13-dioxo-10-[(1-oxododecyl)oxy]-6,8,12-trioxa-3-aza-7-phosphatetracos-1-yl]-1,4,7,10-tetraazacyclododecane-1,4,7-triacetic acid, cpd. 16a Reagents: Compound 15a (600 mg, 0.53 mmol)
Compound 16a (501 mg, 0.53 mmol). Yield 98%.
Analytical Data
HPLC-ELSD: 61.3% (area %)
Mr: 966.16 (C₄₅H₈₄N₅O₁₅P)
¹H- and ¹³C-NMR and MS are compatible with the structure Preparation 4.2b Preparation of 10-[(10R)-7-hydroxy-7-oxido-2,13-dioxo-10-[(1-oxotetradecyl)oxy]-6,8,12-trioxa-3-aza-7-phosphaesacos-1-yl]-1,4,7,10-tetraazacyclododecane-1,4,7-triacetic acid, cpd. 16b Reagents: Compound 15b (2.0 g, 1.68 mmol)
Compound 16b (1.1 g; 1.07 mmol). Yield 63%.
Analytical Data
HPLC-ELSD: 99.9% (area %)
Mr: 1022.26 (C₄₉H₉₂N₅O₁₅P)
¹H- and ¹³C-NMR and MS are compatible with the structure Preparation 5. [[10-[2-(dioctadecylamino)-2-oxoethyl]-1,4,7,10-tetraazacyclododecane-1,4,7-triacetate(3-)]calciate(1-)]calcium (2:1)

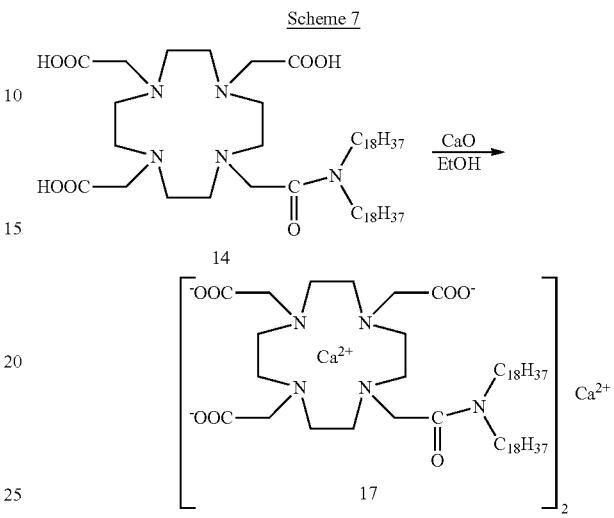

Scheme 7

Calcium oxide CaO (464 mg; 8.30 mmol; 1.5 eq.) was refluxed in ethanol (300 mL) for 1 h then ligand 14 (5 g; 5.5 mmol; 1 eq) was added; the reaction mixture was refluxed for 26 h then filtered to remove the insoluble. The clear solution was concentrated (final volume around 30 mL) obtaining the precipitation of a yellowish solid that was filtered, washed with cold EtOH and H₂O and dried (20 mbar; 30° C.) to give the complex 17 as yellowish solid (3.12 g; 1.71 mmol).
Yield 62.%.
The complex 17 was characterized by NMR, MS and ICP.

Example 1. Preparation of SLN (60R012001L) Containing ICG and DSPE-PEG-2000

The organic phase (O) was prepared by dissolving 401 mg of Epikuron 200® (Cargill Deutschland GmbH, Krefeld, Germany), 100 mg of [1,2-disteroyl-sn-glycero-3-phosphoethanolamine-N-(methoxy(polyethyleneglycol)-2000) ammonium salt DSPE-PEG-2000, 110 mg of complex 17, 450 mg tripalmitin, 50 mg stearic acid and 1.1 mg of ICG in CH₂Cl₂. The organic phase was heated to 35° C. and kept under stirring until complete solubilization of all components. An aqueous phase (W) containing 380 mg of sodium taurocholate, 0.4 mL of 1-butanol and 0.5 mL of water was added to the organic phase. The solution was stirred for 30 min at 35° C. until a stable and transparent microemulsion (W/O) was obtained. Concurrently an aqueous solution W₁ (50 mL) containing 0.24% (weight/volume) Tween 80® (Serva, Heidelberg, Germany) was prepared and heated to 30° C. The microemulsion W/O was added dropwise to the aqueous phase W₁ kept at 30° C. resulting in the multiple emulsion W/O/W₁. The organic solvent was then evaporated at atmospheric pressure maintaining the multiple emulsion under stirring for 45 min. The temperature of the suspension was then lowered to 10° C. (0.25° C./min) to allow crystallization of the lipid core of SLNs. After preparation, the excess of components was removed from the suspension by ultradiafiltration procedure on Labscale™ TFF System and Pellicon XL Filter, 30 kDa 0.005 m² (Merck Millipore, Billerica, Mass.) using an isotonic solution of glucose 5.5% w/v (1 L). Furthermore, possible traces of residual solvent were removed by under vacuum evaporation at room temperature. Finally, the suspension was concentrated to about 8.5 mL and filtered twice using 0.22 µm Sterile Millex®-GS Syringe filters MCE (Millipore, Ireland).

Characterization of the Suspension

The amount of phosphorus present in the final suspension was measured with ICP-MS ELAN 6100 (Perkin Elmer, Waltham, Mass.) after sample digestion in 65% nitric acid with a microwave system (MDS-2000 CEM Corporation). Data are reported in Table G.

ICG amount in the final suspension was measured using a dual-beam Lambda 40 UV-Vis spectrophotometer (Perkin Elmer, Waltham, Mass.). A calibration curve, in a lipidic matrix containing the same molar ratio of the SLNs components, was built using ICG as standard solution in $CHCl_3$:$CH_3OH$ (2:1). From the calibration curve the molar extinction coefficient of ICG was calculated as 229000 $M^{-1}*cm^{-1}$ at its maximum wavelength (800 nm). The analyzed solution was prepared dissolving 7% (v/v) of the ICG-SLNs suspension in the $CHCl_3$:$CH_3OH$ (2:1) solvent mixture.

The incorporation efficiency of ICG in the SLNs was calculated as ratio between ICG in the final suspension compared to the theoretical quantity*100. The ICG incorporation was estimated >90%. The physico-chemical properties of the dispersed nanoparticles, such as average hydrodynamic diameter (z-average) and the polydispersity index (PdI) were measured in NaCl 1 mM at a concentration of P=2 mM by Dynamic Light Scattering (DLS) using Malvern Zeta Sizer Nanoinstrument (NanoZS, Malvern, UK). The surface charge potential (ζ-Potential) was measured at the same condition by Electrophoretic Light Scattering (ELS) by the same instrument. The ICG/P % molar ratio was calculated to be 0.27%. Data are reported in Table F.

The fluorescence quantum yield % (Φ %) was carried out on the FluoroLog-3 1IHR-320 spectrofluorometer equipped with an F-3018 integrating sphere accessory (Horiba Jobin Yvon, Edison N.J.). Detection was performed by photomultiplier tubes PMT-NIR R5509 cooled detector (Hamamatsu photonics, Hamamatsu City, Japan). The Φ% was measured in triplicate with a % average value of 7.7 (SD 0.15).

Differential Scanning calorimetry (DSC) measurement was performed on a calorimeter DSC 4000 Perkin Elmer. ICG-SLNs dispersion was accurately weighted (29.0 mg) into an aluminium crucible and subsequently hermetically closed. The measurement was performed against a water reference crucible. Heating curves were recorded using a scan rate of 5° C./min from 30° C. to 80° C. The experiment is reported in FIG. 9, the onset value was 45.78° C. and ΔH of the formulation was 6.74 J/g. The melting temperature (onset value measured by DSC) is very close to the well-defined polymorphic crystalline form (α) of the triglyceride (±2° C.) (see Chapman D. "The polymorphism of glycerides" 1962 and Windbergs et al. AAPS PharmSciTech, 2009, 10: 1224-1233) and allows to qualitatively define the presence of a crystalline structure in the solid core of the SLNs.

TABLE F

| DLS and ELS characterization. | | | | | |
|---|---|---|---|---|---|
| z-average (nm) | | PdI | | ζ-Potential (mV) | |
| mean | S.D. | Mean | S.D. | Mean | S.D. |
| 55.0 | 0.4 | 0.18 | 0.01 | −13.41 | 1.05 |

TABLE G

| Phosphorus and ICG amount in the final formulation. | | | |
|---|---|---|---|
| Phospholipids (mM) | | ICG (µM) | |
| mean | S.D. | Mean | S.D. |
| 49.8 | 1.2 | 133.9 | 1.1 |

Example 2

Preparation of SLN (60R011013L) Containing ICG and DSPE-PEG-2000

The preparation process was repeated as described in the example 1.

The chemical-physical characterization of the suspension in term of particle size, eta-potential and PdI was made as described in the previous example and the data are reported in Table A.

Example 3

Process for Preparation of SLN (60R012002L) Containing ICG and DSPE-PEG-2000

The preparation process was repeated as described in the example 1.

The chemical-physical characterization of the suspension in term of particle size, eta-potential and PdI was made as described in the example 1 and the data are reported in Table A.

Example 4

Preparation of SLNs (63R011005L) containing ICG, DSPE-PEG-2000 and 1,2-distearyl-sn-glycero-3-phosphoethanolamine-N-[folate (polyethylene glycol)-2000]ammonium salt (DSPE-PEG-2000-folate)

A targeted ICG loaded SLNs was formulated following the same procedure described in example 1 and adding the DSPE-PEG-2000-folate as targeting agent (2 mg) in the organic phase. In the preparation, 402 mg of Epikuron 200®, 99 mg of [1,2-disteroyl-sn-glycero-3-phosphoethanolamine-N-(methoxy(polyethyleneglycol)-2000) ammonium salt DSPE-PEG-2000, 111 mg of complex 17, 450 mg tripalmitin, 50 mg stearic acid and 1.2 mg of ICG were dissolved in $CH_2Cl_2$. The aqueous phase (W) contained 382 mg of sodium taurocholate, 0.4 mL of 1-butanol and 0.5 mL of water. The suspension was concentrated to about 8.5 mL.

The physico-chemical characterization of the suspension was made as described in example 1 and the data are reported in Tables H and I. The ICG/P molar ratio was calculated to be 0.26%. The % ICG incorporation was estimated ~90%. The fluorescence quantum yield % was 7.6 (SD 0.3). DSC analysis was carried out on 31.2 mg of formulation. The onset value was 45.56° C. whereas ΔH of the formulation was 7.13 J/g.

TABLE H

DLS and ELS characterization.

| z-average (nm) | | PdI | | ζ-Potential (mV) | |
|---|---|---|---|---|---|
| mean | S.D. | mean | S.D. | mean | SD |
| 63.0 | 0.7 | 0.13 | 0.02 | −13.87 | 0.85 |

TABLE I

Phosphorus and ICG amount in the final formulation

| Phospholipids (mM) | | ICG (μM) | |
|---|---|---|---|
| mean | S.D. | Mean | SD |
| 58.3 | 1.1 | 151.34 | 2.20 |

FIG. 10 shows the DSC curve of the SLNs of this example. The melting temperature (onset value measured by DSC) is close to the well defined polymorphic crystalline form (α) of the triglyceride (±2° C.) (see Chapman D. "The polymorphism of glycerides", Chem. Rev., 1962, 62: 433-456 and Windbergs et al. AAPS PharmSciTech, 2009, 10: 1224-1233) and allows to qualitatively define the presence of a crystalline structure in the solid core of the SLNs.

The colloidal stability of the formulation in term of surface charge, PdI and ζ-potential were measured until 90 days keeping the formulation in the dark, at 4° C. Measurements were carried out at 25° C. with Malvern Instrument (Zetasizer Nano ZS), diluting the sample in NaCl 1 mM. Results are listed in Table D.

Example 5. Preparation of SLNs (63R011001L) Containing ICG and DSPE-PEG-2000 and 1,2-distearyl-sn-glycero-3-phosphoethanolamine-N-[folate (polyethylene glycol)-2000] ammonium salt (DSPE-PEG-2000-folate)

A targeted ICG loaded SLNs was formulated following the same procedure described in example 1 and adding the DSPE-PEG-2000-folate as targeting agent (1 mg) in the organic phase. In the preparation, 202 mg of Epikuron 200®, 50 mg of DSPE-PEG-2000, 56 mg of complex 17, 225 mg tripalmitin, 25 mg stearic acid and 2 mg of ICG were dissolved in $CH_2Cl_2$ (2 mL). The aqueous phase W (0.25 mL) contained 175 mg of sodium taurocholate, 0.2 mL of 1-butanol. The aqueous phase $W_1$ (25 mL) contained Tween 80® 0.24% w/v. The suspension was concentrated to about 10 mL.

The chemical-physical characterization of the suspension in term of particle size, ζ-potential and PdI was made as described in the example 1 and the data are reported in Table A.

Example 6. Preparation of SLNs (63R011002L) Containing ICG and DSPE-PEG-2000 and 1,2-distearyl-sn-glycero-3-phosphoethanolamine-N-[folate (polyethylene glycol)-2000] ammonium salt (DSPE-PEG-2000-folate)

A targeted ICG loaded SLNs was formulated following the same procedure described in example 1 and adding the DSPE-PEG-2000-folate as targeting agent (1 mg) in the organic phase. In the preparation, 202 mg of Epikuron 200®, 52 mg of DSPE-PEG-2000, 56 mg of complex 17, 225 mg tripalmitin, 25 mg stearic acid and 2 mg of ICG were dissolved in $CH_2Cl_2$ (2 mL). The aqueous phase W (0.250 mL) contained 190 mg of sodium taurocholate, 0.2 mL of 1-butanol. The aqueous phase $W_1$ (25 mL) contained Tween 80® 0.24% w/v. The suspension was concentrated to about 8 mL.

The chemical-physical characterization of the suspension in term of particle size, ζ-potential and PdI was made as described in the previous example and the data are reported in Table A.

Example 7. UV-Vis Spectra of ICG-Loaded SLNs Suspension and Free ICG Solution for J-Aggregates Evaluation UV-Vis spectra of ICG-loaded SLNs suspension, prepared as described in the example 4, were recorded after the end of the formulation date, 90 and 120 days later keeping the suspension at store condition. After 120 days the absorbance was recovered at 96% with respect to the initial value (FIG. 4 A).

A solution of ICG (0.14 mg/mL) was prepared in glucosate (5.5%) solution. The sample was diluted before the Uv-Vis analysis and the absorption behaviour was evaluated from 300 to 950 nm until 15 days (FIG. 4 B).

Example 8. Photobleaching Experiment

The photobleaching experiment was performed by the exposition of free ICG aqueous solution and the ICG loaded SLNs suspension to a 785 nm laser radiation The fluorescence emissions were collected by NIR fluorescent imaging system (Pearl® Impulse system by LI-COR Biosciences). The amount of ICG (0.23 nmol of ICG and 0.036 nmol of ICG loaded SLNs having fluorescence quantum yield of 5.6%) were adjusted to display initial comparable fluorescence emission signal.

Figure 2:
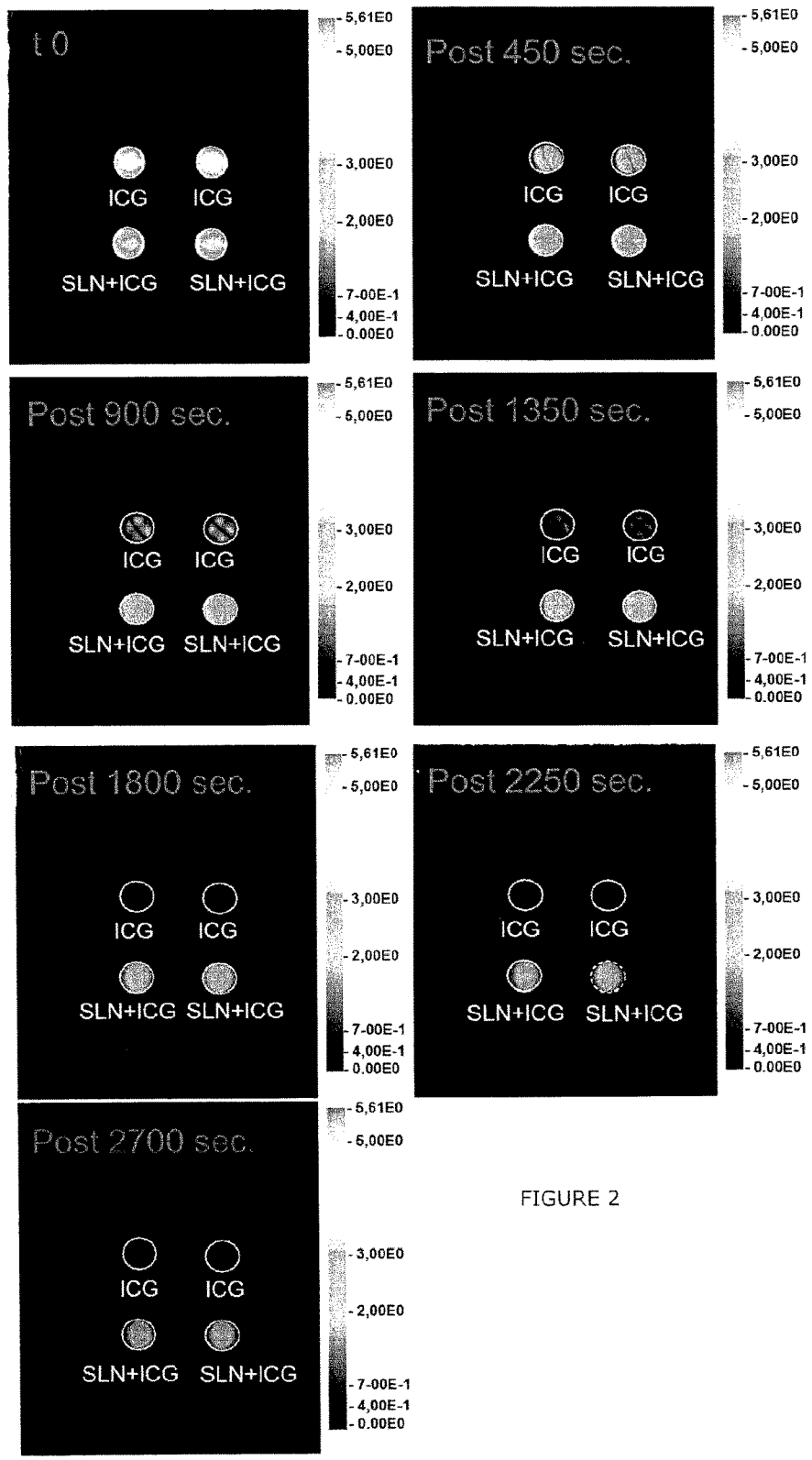
FIG. 2 represents the results of ICG and ICG-loaded SLNs photobleaching experiments.

Then, the experiment was carried out in duplicate at 37° C. irradiating both samples for 3 sec and keeping the samples in the dark for 1 sec. This sequence was repeated in continuous for 1 h. Results are shown in FIG. 2.

Example 9. Long Term Stability of ICG Loaded SLNs by UV-Vis Measurements at its Maximum Absorption Wavelength ICG amount in the final formulation was measured as described in the example 1 using a dual-beam Lambda 40 UV-Vis spectrophotometer (Perkin Elmer, Waltham, Mass.). Thermal stability was analyzed by keeping the samples in the dark at storage condition (4° C.) for 90 days and by measuring the absorption maximum at 800 nm after ICG loaded SLNs (prepared as described in the example 4) dissolution in an organic solvent mixture ($CHCl_3$:MeOH; 2:1).

Example 10. Demonstration of the Targeting Properties of Targeted ICG Loaded SLNs by Biolayer Interferometry Biolayer interferometry (OCTET QK, FortéBio) was performed on two different batches of targeted and untargeted ICG-loaded SLNs (prepared as described in the example 5 and 2 respectively) towards the antibody (Mab FA2) anti-Folic acid. In the experiments, a biosensors were coated via protein A interaction with a monoclonal antibody (Mab FA2) anti-Folic acid by incubation for 6 minutes at RT. Before the analysis, biosensors were washed with PBS solution and immediately dipped in a 96-multiwell plate containing targeted ICG loaded SLNs diluted suspension kept under mixing. After 300 s of incubation, the sensors were moved to a well containing phosphate buffered saline (PBS) solution to visualize the dissociation curves. The specificity of the binding between the MAb FA2 with the F-ICG loaded SLNs was confirmed comparing the untargeted ICG loaded SLNs (negative control) analysis performed in the same way. The experiment is reported in FIG. 5 (the dotted line separates the association from the dissociation curves).

Example 11. In Vivo and Ex-Vivo Evaluation of Tumor Targeting by Fluorescence Imaging F-ICG-SLNs and ICG-SLNs, formulated in the example 5 and 2 respectively were evaluated on an ovarian carcinoma xenograft model using IGROV-1 cell line subcutaneously injected in the right flank of Balb/C nu/nu mice. The mice (n=6) were selected by pre-treatment with free ICG dye for the evaluation of the degrees of vascularisation. In this way, animals were consistently distributed in two groups. The acquired fluorescence signal was collected in a region of interest drawn around the tumor area and referred to the background fluorescence of the muscle as (tumor SI–muscle SI)/muscle SI. The in vivo data analysis at 30 min, 4 h and 24 h after the injection of 15 nmoles of ICG/mouse resulted in a higher tumor signal intensity of F-ICG-SLN with respect to the untargeted one. After 24 h measured fluorescence signal was 5.1 a.u. (SD 2.9), whereas in the case of untargeted ICG loaded SLNs administration, the fluorescence signal was 1.7 (SD 0.2). Organs were excised and tissued were analysed for ex vivo fluorescence quantification (FIGS. 6 and 7).

The invention claimed is:
1. A solid lipid nanoparticle comprising:
   a) a solid lipid core comprising at least a glyceride and/or at least a fatty acid;
   b) a mixture of amphiphilic components forming a shell around said core a);
   c) an alkaline-earth complex with a compound of formula I:

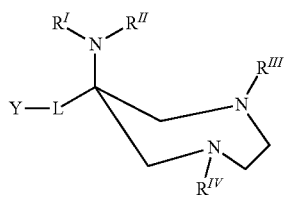

(I)

wherein:
   Y is a group of formula Y'—NH— or (Y')$_2$—N—, wherein Y', which in case of (Y')$_2$—N— can be the same or different, is selected from the group consisting of: linear or branched, saturated or unsaturated C$_{12}$-C$_{20}$ alkyl group; C$_1$-C$_{10}$ alkyl group, optionally interrupted by a phosphate group —O—(HO—P=O)—O—, or optionally substituted by one or more atoms or groups selected from the group consisting of: OH, COOR$_1$, oxycarbonyl-(C$_{12}$-C$_{18}$)alkyl and oxycarbonyl-(C$_{12}$-C$_{18}$)alkenyl; wherein R$_1$ is selected from the group consisting of hydrogen H and a linear or branched C$_1$-C$_4$ alkyl group; and a monophosphate ester of a substituted or partially substituted glycerol, having at least one functional group of said glycerol esterified with an aliphatic fatty acid with saturated or unsaturated carbon chains, and the other two functions of phosphoric acid being either free or salified with alkali or earth alkali metals;
   L is a bivalent linker selected from the group consisting of: aliphatic C$_3$-C$_{10}$, or linear or branched C$_1$-C$_6$ alkanediyl, alkenediyl, alkynediyl, optionally interrupted with one or more atoms or atom groups selected from the group consisting of: —C=O—, —C=S—, —NR$_1$—, —COO—, —OCO—, —NR$_1$CO—, —CONR$_1$—, —O— and —S—, wherein R$_1$ is as defined above;
   R$^{I-IV}$, are each, independently, a —R$_2$—COOR$_3$, wherein R$_2$ is a C$_1$-C$_6$ linear or branched alkyl, R$_3$ is H or a pharmaceutically acceptable cation;
   d) at least a fluorescent dye selected from the group consisting of: a cyanine fluorescent dye and/or a polyetherocyclic compound selected from: coumarin, pyrano, quinoline, pyranoquinoline, indole and pyranoindole derivates in acid form or a pharmaceutically acceptable salt thereof.

2. The nanoparticle according to claim 1, wherein said alkaline-earth complex compound of formula I is as defined in claim 1 and wherein:
   Y', which in case of (Y')$_2$—N— can be the same or different, is selected from the group consisting of: linear or branched, saturated or unsaturated C$_{16}$-C$_{18}$ alkyl group; C$_4$-C$_6$ alkyl group interrupted by a phosphate group —O—(HO—P—O)—O— and/or optionally substituted by one or more atoms or groups selected from the group consisting of: oxycarbonyl-(C$_{12}$-C$_{18}$)alkyl and oxycarbonyl-(C$_{12}$-C$_{18}$)alkenyl; and a monophosphate ester of a substituted or partially substituted glycerol, having at least one functional group of said glycerol esterified with an aliphatic fatty acid wherein said aliphatic fatty acid is a C$_{14}$-C$_{20}$ carboxylic acid with saturated or unsaturated carbon chains, and the other two functions of phosphoric acid being either free or salified with alkali or earth alkali metals; being L and R$^{I-IV}$ as defined above.

3. The nanoparticle according to claim 2 where in the alkaline-earth complex with a compound of formula I wherein Y' is a C$_4$-C$_6$ alkyl group interrupted by a phosphate group —O—(HO—P—O)—O—, further substituted by at least two atoms or groups selected from the group consisting of: oxycarbonyl-(C$_4$-C$_{16}$)alkyl and oxycarbonyl-(C$_{14}$-C$_{16}$) alkenyl.

4. The nanoparticle according to claim 1, further comprising:
   e) a hydrophilic polymeric function covalently linked to said shell b) having the function of stealth agent.

5. The nanoparticle according to claim 4, further comprising:
   f) a molecular targeting moiety for the specific binding towards one pathology-related biological marker, said moiety being linked either to said core shell b) or said hydrophilic polymeric function e).

6. The nanoparticle according to claim 1, wherein said solid lipid core
   a) comprises at least one glyceride, and/or at least one fatty acid or a mixture thereof, said at least one glyceride or fatty acid or an ester thereof is or are in the solid form at room temperature and at body temperature.

7. The nanoparticle according to claim 6, wherein said glyceride is selected from the group consisting of a monoglyceride, a diglyceride and a triglyceride having a saturated or unsaturated, linear or branched $C_{12}$-$C_{24}$ acyl chain, wherein in case of di- and triglyceride, the acyl chains can be the same or different; said fatty acid, or an ester thereof; has a saturated or unsaturated, linear or branched $C_{12}$-$C_{24}$ carbon chain; and said core optionally comprises esters $C_{12}$-$C_{24}$ fatty acids with $C_{12}$-$C_{24}$ fatty alcohols.

8. The nanoparticle according to claim 7, wherein said core a) comprises tripalmitin and/or stearic acid.

9. The nanoparticle according to claim 1, wherein said mixture of amphiphilic components b) comprises a component selected from the group consisting of phospholipids, lysolipids and sphingolipids having linear or branched, saturated or unsaturated $C_6$-$C_{24}$ hydrocarbon chains; and optionally at least one of cholesterol and steroid derivatives, glycolipids, fatty acids, fatty alcohols and dialkyl ethers, non-ionic surfactant selected from sorbitan derivatives, di- and tri-esters of saturated and unsaturated fatty acid derivatives from $C_6$-$C_{24}$ carbon atoms and ethoxylated analogue thereof, mono or oligo-glycosides and ethoxylated analogues thereof and glycerol mono, di- and tri-esters soluble at room and at body temperature.

10. The nanoparticle, according to claim 9, wherein said mixture of amphiphilic components comprises phosphatidylcholine from soy lecithin.

11. The nanoparticle according to claim 9, wherein said non-ionic surfactant is polyoxyethylene sorbitan monooleate.

12. The nanoparticle according to claim 4, wherein said hydrophilic polymer e) is selected from the group consisting of functionalized poloxamer, polysiloxanes, polyalkyl polyether, polyglycerine, polyvinilalcohol and a polyethyleneglycol, optionally covalently linked to a phospholipidic moiety.

13. The nanoparticle according to claim 1, wherein said fluorescent dye is Indocyanine Green of formula

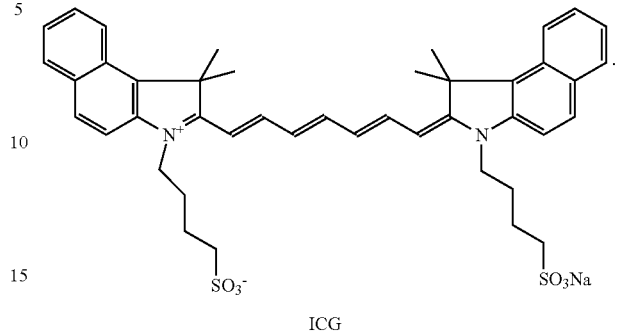

ICG

14. The nanoparticle according to claim 5, wherein said molecular targeting moiety f) is a tumor targeting ligand selected from the group consisting of cell surface receptor, proteins, aptamers, peptides and polypeptides, vitamins, antibodies or fragments thereof and carbohydrates.

15. The nanoparticle of claim 1 wherein the alkaline-earth complex with a compound of formula I is selected from the group consisting of:

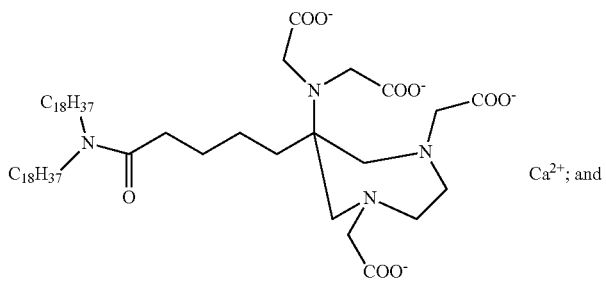

c.1.

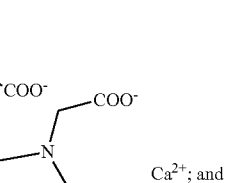

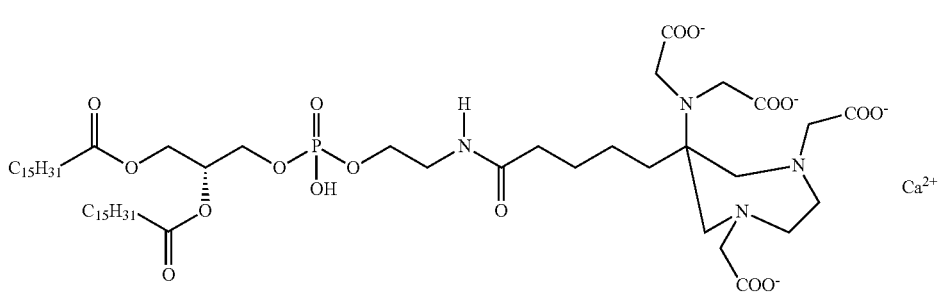

c.4

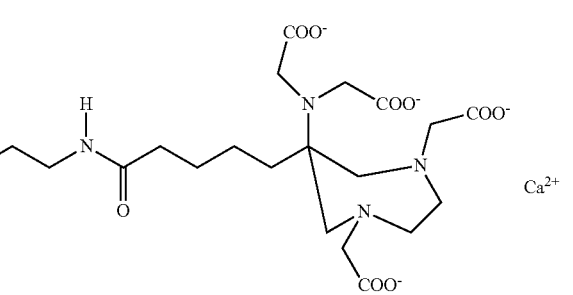

16. A pharmaceutical composition comprising the nanoparticle of claim 1.

17. A process for the preparation of the nanoparticle of claim 1 comprising the following steps:

i. preparing an organic phase (O) by dissolving in a water immiscible or low-miscible organic solvent, a lipid substance or substances, which will form the solid lipid crystalline core a), the amphiphilic component b) and an alkaline-earth complex with a compound of formula I, c), as defined in claim 1:

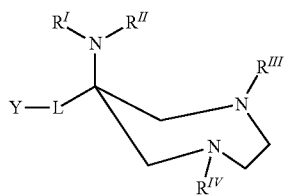 (I)

the fluorescent dye d);
ii. preparing a first aqueous solution (W) by dissolving one or more hydrophilic surfactants and optionally co-surfactants components;
iii. mixing said organic phase (O) of step i) with said first aqueous solution (W) of step ii) and stirring until a stable W/O micro-emulsion is formed;
iv. said W/O micro-emulsion obtained in step iii) is subsequently added to a second aqueous solution ($W_1$) which can contain at least a surfactant, to provide a W/O/$W_1$ multiple emulsion;
v. stripping said organic solvent from the multiple emulsion by evaporation to provide a suspension;
vi. cooling down the suspension obtained in step v) to provide the complete crystallization of said solid core a);
vii. washing said dispersion obtained in step vi) from the excess of the components;
viii. optionally storing said dispersion obtained in step vii) in aqueous phase or as a solid phase after water removal.

18. The process according to claim 17, wherein said organic solvent in step i) has a boiling point from 20° C. to 70° C.

19. The process according to claim 18, wherein said solvent is selected from the group consisting of methylene chloride, 1,2-dichloroethane, chloroform, diethyl ether, ethylacetate, methylacetate, ethyl formate and a mixture thereof.

20. The process according to claim 19 wherein in said step ii)
the hydrophilic surfactant is selected from the group consisting of: cholic acid, taurocholic acid, taurodeoxycholic acid, a salt thereof, and a derivative thereof; and
the co-surfactant is selected in the group consisting of: 1-butanol and 1-hexanol.

21. The process according to claim 17 wherein in said step iv) the surfactant is a sorbitan derivative.

22. A method of diagnostic imaging comprising:
administering to a subject an effective amount of the pharmaceutical composition of claim 16; and
subjecting said subject to a suitable diagnostic imaging method.

23. The method of claim 22, wherein the diagnostic imaging method is selected from the group consisting of:
real-time imaging guided surgery; and
tumor detection and/or lymph nodes mapping in clinical fluorescence imaging applications.

* * * * *

UNITED STATES PATENT AND TRADEMARK OFFICE
CERTIFICATE OF CORRECTION

PATENT NO. : 10,251,960 B2
APPLICATION NO. : 14/894505
DATED : April 9, 2019
INVENTOR(S) : Simona Ghiani et al.

Page 1 of 1

It is certified that error appears in the above-identified patent and that said Letters Patent is hereby corrected as shown below:

In the Claims

Column 56, Line 32, Claim 2, the phrase "group -O-(HO-P-O)-O- and/or" should read
– group -O-(HO-P=O)-O- and/or –.

Column 56, Line 47, Claim 3, the phrase "group -O-(HO-P-O)-O-, further" should read
– group -O-(HO-P=O)-O-, further –.

Column 56, Line 49, Claim 3, the phrase "oxycarbonyl-(C4-C16)alkyl" should read
– oxycarbonyl-(C14-C16)alkyl –.

Column 57, Line 6, Claim 7, the phrase "an ester thereof;" should read – an ester thereof, –.

Column 57, Line 25, Claim 9, the phrase "analogues thereof and" should read – analogues thereof, and –.

Signed and Sealed this
Twenty-second Day of October, 2019

Andrei Iancu
*Director of the United States Patent and Trademark Office*